US009260691B2

(12) United States Patent
Youil et al.

(10) Patent No.: US 9,260,691 B2
(45) Date of Patent: Feb. 16, 2016

(54) METHODS RELATING TO AN ATTENUATED MYCOPLASMA

(75) Inventors: Rima Youil, Port Melbourne (AU); Youssef Abs El-Osta, Glenroy (AU)

(73) Assignee: BIOPROPERTIES PTY LTD, Ringwood, Victoria (AU)

( * ) Notice: Subject to any disclaimer, the term of this patent is extended or adjusted under 35 U.S.C. 154(b) by 0 days.

(21) Appl. No.: 13/697,714

(22) PCT Filed: May 19, 2011

(86) PCT No.: PCT/AU2011/000584

§ 371 (c)(1), (2), (4) Date: Mar. 27, 2013

(87) PCT Pub. No.: WO2011/143706

PCT Pub. Date: Nov. 24, 2011

(65) Prior Publication Data

US 2013/0243819 A1 Sep. 19, 2013

(30) Foreign Application Priority Data

May 19, 2010 (AU) ................................ 2010902198

(51) Int. Cl.

| | |
|---|---|
| ***A61K 39/04*** | (2006.01) |
| ***C07K 14/35*** | (2006.01) |
| ***C12N 15/00*** | (2006.01) |
| ***C12Q 1/00*** | (2006.01) |
| ***C12N 1/36*** | (2006.01) |
| ***A61K 39/02*** | (2006.01) |
| ***C07K 14/30*** | (2006.01) |
| ***C12Q 1/68*** | (2006.01) |
| *A61K 39/00* | (2006.01) |

(52) U.S. Cl.

CPC .............. *C12N 1/36* (2013.01); *A61K 39/0241* (2013.01); *C07K 14/30* (2013.01); *C12Q 1/689* (2013.01); *A61K 2039/522* (2013.01); *C12Q 2600/156* (2013.01)

(58) Field of Classification Search

None

See application file for complete search history.

(56) References Cited

U.S. PATENT DOCUMENTS

| | | | | |
|---|---|---|---|---|
| 6,585,981 | B1 | 7/2003 | Pijoan | |
| 2009/0117152 | A1 * | 5/2009 | Chu et al. | 424/201.1 |

FOREIGN PATENT DOCUMENTS

| | | | |
|---|---|---|---|
| CN | 101420975 | A | 4/2009 |
| WO | WO 00/18434 | | 4/2000 |
| WO | WO 02/10343 | | 2/2002 |
| WO | WO2009/035644 | A1 | 3/2009 |
| WO | WO2009/036241 | A1 | 3/2009 |
| WO | WO 2010/094064 | | 8/2010 |
| WO | WO 2010/132932 | | 11/2010 |

OTHER PUBLICATIONS

Pagani et al. 2004 (Genomic variants in exons and introns: identifying the splicing spoilers; Nature Reviews 5:389-396).* de Castro et al. 2006 (Variable number of tandem amino acid repeats in adhesion-related CDS products in Mycoplasma hyopneumoniae strains; Veterinary Microbiology 116:258-269).*

Bauman et al. 2011 (Chapter 17: Immunization and Immune Testing; in Microbiology with Diseases by Body System; published by Benjamin Cummings, ISBN-13: 9780321712714, pp. 490-509).*

English Translation of Chinese Examination Report received in Application No. 201180024822.8 dated Apr. 25, 2014.

Deli, et al., "A Study on Clinical Application of Polymerase Chain Reaction in Detection of Mycoplasma Pneumoniaex," *Chinese Journal of Pediatrics,* 32(5):296-297 (1994).

Minguang, et al., "Detection and Analysis of Trachomatis and Mycoplasm in the Patients with Non-Bacterial Prostatitis," *Zhejiang Journal of Preventive Medicine,* 15(2):9-10 (2003).

European Search Report received in Application No. 11782772.5—1410/2571980 dated Jan. 29, 2014.

N.F. Friss, "Some Recommendations Concerning Primary Isolation of Mycoplasma suipneumoniae and Mycoplasma flocculare—A Survey", From the State Veterinary Serum Laboratory, Copenhagen, Nor. Vet-Med., 1975, 27, pp. 337-339.

Lloyd & Etheridge, "The Pathological and Serological Response Induced in Pigs by Parenteral Inoculation of *Mycoplasma Hyopneumoniae*", (1981) J. Comp. Path. 91:77-83.

Nonamura and Imada, "Temperature—Sensitive Mutant of Mycoplasma synoviae" (1982) Avian Diseases, vol. 26, No. 4 (Oct.-Dec. 1982), pp. 763-775.

De Castro et al., "Variable number of tandem amino acid repeats in adhesion-related CDS products in *Mycoplasma hyopneumoniae* strains", Veterinary microbiology, 2006, vol. 116, No. 4, pp. 258-269.

Ferreira and de Castro "A preliminary survey of *M. hyopneumoniae* virulence factors based on comparative genomic analysis", Genetics and Molecular Biology, 30, 1, pp. 245-255, (2007).

Madsen, M.L. et al., Array-Based Genomic Comparative Hybridization Analysis of Field Strains of *Mycoplasma hyopneumoniae,* Journal of Bacteriology, Nov. 2007, vol. 189, No. 22, pp. 7977-7982.

Szczepanek et al., "Comparative Genomic Analyses of Attenuated Strains of *Mycoplasma gallisepticum*", Infection and Immunity, Apr. 2010, vol. 78, No. 4, pp. 1760-1771.

PCT/AU2011/000584 International Search Report dated Jul. 21, 2011 (7 pages).

PCT/AU2011/000584 International Preliminary Report on Patentability dated Aug. 24, 2012 (15 pages).

* cited by examiner

*Primary Examiner* — Gary Nickol

*Assistant Examiner* — Mary Lyons

(74) *Attorney, Agent, or Firm* — Brinks Gilson & Lione

(57) ABSTRACT

The present invention provides a method for identifying or generating an attenuated *mycoplasma* bacterium, which bacterium comprises a mutation in at least one gene as listed and use of the bacterium in a vaccine for eliciting protective immunity against *mycoplasma* or for detecting infection by said bacterium.

5 Claims, 18 Drawing Sheets

Figure 1A - 1

| Number | | | | Nucleotide Base | | | | Gene | Nature of mutation |
|---|---|---|---|---|---|---|---|---|---|
| J | LKR | MTR | P12 | J | LKR | MTR | P12 | | |
| 3075 | 3072 | 3072 | 3074 | A | A | Δ A | Δ A | GidA gene [tRNA uridine 5-carboxymethylaminomethyl modification enzyme YP_278808.1 | Frameshift |
| 7324 | 7316 | 7311 | 7318 | A | A | Δ A | Δ A | Hypothetical protein YP_278812.1 | Frameshift |
| 17143 | 17119 | 17111 | 17126 | T | T | Δ T | Δ T | Intergenic | |
| 19386 | 19361 | 19350 | 19367 | T | T | Δ T | Δ T | Putative ABC transporter ATP binding YP_278823.1 | Frameshift |
| 31773 | 31738 | 31723 | 31754 | T | T | Δ T | Δ T | Isoleucyl tRNA synthetase YP_278833.1 | Frameshift |
| 48566 | 48512 | 48490 | 48597 | A | A | Δ A | Δ A | GTPase ObgE YP_278842.1 | Frameshift |
| 48881 | 48827 | 48804 | 48852 | A | A | Δ A | Δ A | Intergenic | |
| 51166 | 51112 | 51083 | 51136 | A | A | Δ A | Δ A | DNA polymerase IV YP_278846.1 | Frameshift |
| 59567 | 59498 | 59468 | 59529 | T | T | Δ T | Δ T | Intergenic | |
| 66347 | 66274 | 66236 | 66302 | A | A | Δ A | Δ A | Intergenic | |
| 75037 | 74954 | 74906 | 74985 | A | A | Δ A | Δ A | Hypothetical protein YP_278865.1 | Frameshift |
| 79461 | 79377 | 79326 | 79407 | T | T | Δ T | Δ T | Excinuclease ABC subunit C YP_278867.1 | Frameshift |
| 86810 | 86721 | 86667 | 86749 | T | T | Δ T | Δ T | Hypothetical protein YP_278873.1 | Frameshift |
| 89715 | 89626 | 89570 | 89653 | A | A | Δ A | Δ A | Intergenic | |
| 94740 | 94647 | 94587 | 94671 | A | A | Δ A | Δ A | Intergenic | |
| 94742 | 94649 | 94589 | 94673 | T | T | Δ T | Δ T | Intergenic | |
| 104392 | 104281 | 104212 | 104297 | T | T | Δ T | Δ T | Intergenic | |
| 104393 | 104282 | 104213 | 104298 | A | A | Δ A | Δ A | Intergenic | |
| 117390 | 117262 | 117188 | 117282 | A | A | Δ A | Δ A | Intergenic | |
| 118681 | 118553 | 118478 | 118572 | A | A | Δ A | Δ A | Hypothetical protein YP_278896.1 | Frameshift |
| 118716 | 118588 | 118512 | 118606 | A | A | Δ A | Δ A | Hypothetical protein YP_278896.1 | Frameshift |
| 120943 | 120810 | 120729 | 120827 | A | A | Δ A | Δ A | Intergenic | |
| 125147 | 125010 | 124925 | 125028 | A | A | Δ A | Δ A | Putative outer membrane protein P95 YP_278901.1 | Frameshift |
| 131715 | 131576 | 131486 | 131595 | A | A | Δ A | Δ A | Triosephosphate isomerase YP_278904.1 | Frameshift |
| 133772 | 133626 | 133537 | 133645 | T | T | Δ T | Δ T | Intergenic | |
| 136750 | 136600 | 136511 | 136620 | T | T | Δ T | Δ T | Hypothetical protein YP_278906.1 | Frameshift |
| 143404 | 143252 | 143156 | 143272 | T | T | Δ T | Δ T | Intergenic | |
| 143493 | 143339 | 143243 | 143359 | A | A | Δ A | Δ A | Intergenic | |
| 147361 | 147194 | 147100 | 147214 | A | A | Δ A | Δ A | Intergenic | |
| 153557 | 153372 | 153282 | 153379 | T | T | Δ T | Δ T | Intergenic | |

Amended

Figure 1A - 2

| Number | | | | Nucleotide Base | | | | Gene | Nature of mutation |
|---|---|---|---|---|---|---|---|---|---|
| J | LKR | MTR | P12 | J | LKR | MTR | P12 | | |
| 155557 | 155366 | 155275 | 155373 | A | A | Δ A | Δ A | Hypothetical protein YP_278917.1 | Frameshift |
| 157051 | 156860 | 156767 | 156866 | A | A | Δ A | Δ A | Hypothetical protein YP_278919.1 | Frameshift |
| 163824 | 163618 | 163519 | 163631 | A | A | Δ A | Δ A | Uracil-DNA glycosylase YP_278929.1 | Frameshift |
| 170370 | 170152 | 170050 | 170169 | T | T | Δ T | Δ T | Intergenic | |
| 178555 | 178332 | 178222 | 178349 | T | T | Δ T | Δ T | Putative chromate transport protein YP_278943.1 | Frameshift |
| 183981 | 183755 | 183643 | 183771 | T | T | Δ T | Δ T | Hypothetical protein YP_278948.1 | Frameshift |
| 187424 | 187191 | 187078 | 187208 | A | A | Δ A | Δ A | Intergenic | |
| 187449 | 187216 | 187103 | 187233 | A | A | Δ A | Δ A | Intergenic | |
| 190701 | 190467 | 190352 | 190484 | A | A | Δ A | Δ A | Putative ABC transporter ATP binding and permease protein YP_278958.1 | Frameshift |
| 212677 | 212420 | 212297 | 212445 | T | T | Δ T | Δ T | 50S Ribosomal protein L3 YP_278992.1 | |
| 214047 | 213787 | 213658 | 213817 | A | A | Δ A | Δ A | Hypothetical protein YP_278995.1 | Frameshift |
| 214362 | 214096 | 213969 | 214129 | A | A | Δ A | Δ A | Intergenic | |
| 226284 | 226068 | 225865 | 226047 | T | T | Δ T | Δ T | Hypothetical protein YP_279003.1 | Frameshift |
| 234616 | 234334 | 234188 | 234371 | A | A | Δ A | Δ A | Hypothetical protein YP_279009.1 | Frameshift |
| 235499 | 235215 | 235066 | 235251 | T | T | Δ T | Δ T | Intergenic | |
| 246806 | 246518 | 246360 | 246550 | A | A | Δ A | Δ A | Intergenic or putative lipoprotein YP_279015.1 | |
| 246808 | 246520 | 246362 | 246552 | A | A | Δ A | Δ A | Putative lipoprotein YP_279015.1 | Frameshift |
| 252401 | 252109 | 251949 | 252141 | T | T | Δ T | Δ T | Ribonucleotide-disulphate reductase subunit alpha YP_279017.1 | Frameshift |
| 271614 | 271294 | 271122 | 271333 | T | T | Δ T | Δ T | Hypothetical protein YP_279032.2 | Frameshift |
| 293668 | 293332 | 293149 | 293374 | A | A | Δ A | Δ A | Hypothetical protein YP_279046.1 | Frameshift |
| 300092 | 299752 | 299563 | 299795 | A | A | Δ A | Δ A | Thymidylate kinase YP_279053.1 | Frameshift |
| 300098 | 299758 | 299569 | 299801 | A | A | Δ A | Δ A | Thymidylate kinase YP_279053.1 | Frameshift |
| 300772 | 300432 | 300240 | 300474 | A | A | Δ A | Δ A | DNA polymerase III subunit delta YP_279054.1 | Frameshift |
| 305732 | 305384 | 305184 | 305426 | T | T | Δ T | Δ T | DNA ligase YP_279060.1 | Frameshift |
| 328394 | 327999 | 327800 | 328060 | A | A | Δ A | Δ A | CDP-diacylglycerol-glycerol-3-phosphate-3-phosphatidyal transferase YP_279075.1 | Frameshift |

Amended

Figure 1A - 3

| Number | | | | Nucleotide Base | | | | Gene | Nature of mutation |
|---|---|---|---|---|---|---|---|---|---|
| J | LKR | MTR | P12 | J | LKR | MTR | P12 | | |
| 377689 | 377235 | 377020 | 377319 | T | T | Δ T | Δ T | putative ISMHp1 transposase YP_279110.1 | Frameshift |
| 389842 | 389376 | 389157 | 389461 | T | T | Δ T | Δ T | hypothetical protein YP_279121.1 | Frameshift |
| 393661 | 393192 | 392955 | 393271 | A | A | Δ A | Δ A | Intergenic | |
| 410563 | 410082 | 409835 | 410164 | T | T | Δ T | Δ T | Intergenic | |
| 412710 | 412226 | 411976 | 412307 | T | T | Δ T | Δ T | Hypothetical protein YP_279136.1 | Frameshift |
| 413717 | 413232 | 412980 | 413313 | A | A | Δ A | Δ A | Hypothetical protein YP_279138.1 | Frameshift |
| 426313 | 425818 | 425552 | 426313 | A | A | Δ A | Δ A | Intergenic | |
| 426326 | 425831 | 425563 | 425910 | T | T | Δ T | Δ T | Intergenic | |
| 431650 | 431149 | 430879 | 431226 | A | A | Δ A | Δ A | Intergenic | |
| 431669 | 431168 | 430898 | 431244 | T | T | Δ T | Δ T | Intergenic | |
| 437234 | 436729 | 436455 | 436804 | T | T | Δ T | Δ T | putative ABC transport system permease protein p69-like YP_279157.1 | Frameshift |
| 442618 | 442107 | 441827 | 442184 | A | A | Δ A | Δ A | putative lipoprotein YP_279161.1 | Frameshift |
| | | | | | | | | | |
| 475493 | 474937 | 474655 | 475032 | A | A | Δ A | Δ A | hypothetical proteinYP_279182.1 | Frameshift |
| 477621 | 477066 | 476785 | 477160 | A | A | Δ A | Δ A | Intergenic | |
| 477622 | 477067 | 476786 | 477161 | A | A | Δ A | Δ A | Intergenic | |
| 479170 | 478611 | 478329 | 478704 | T | T | Δ T | Δ T | Intergenic | |
| 485869 | 485296 | 485023 | 485399 | T | T | Δ T | Δ T | hypothetical protein YP_279196.1 | Frameshift |
| 486911 | 486337 | 486063 | 486440 | A | A | Δ A | Δ A | hypothetical protein YP_279196.1 | Frameshift |
| 491786 | 491200 | 490917 | 491301 | A | A | Δ A | Δ A | Intergenic | |
| 502594 | 501992 | 501705 | 502097 | T | T | Δ T | Δ T | Intergenic | |
| 512112 | 511491 | 511193 | 511596 | T | T | Δ T | Δ T | hypothetical protein YP_279217.1 | Frameshift |
| 519298 | 518667 | 518366 | 518771 | A | A | Δ A | Δ A | transketolase YP_279223.1 | Frameshift |
| 524764 | 524126 | 523821 | 524234 | T | T | Δ T | Δ T | Intergenic | |
| 534108 | 533459 | 533152 | 533572 | T | T | Δ T | Δ T | hypothetical protein YP_279235.1 | Frameshift |
| 539244 | 538589 | 538279 | 538702 | A | A | Δ A | Δ A | Intergenic | |
| 558831 | 558174 | 557849 | 558286 | T | T | Δ T | Δ T | hypothetical protein YP_279242.1 | Frameshift |
| 564250 | 563590 | 563258 | 563701 | T | T | Δ T | Δ T | Intergenic | |
| 569870 | 569202 | 568872 | 569320 | A | A | Δ A | Δ A | hypothetical protein YP_279247.1 | Frameshift |
| 586142 | 585455 | 585116 | 585569 | T | T | Δ T | Δ T | Intergenic | |
| 590751 | 590056 | 589710 | 590170 | A | A | Δ A | Δ A | hypothetical protein YP_279262.1 | Frameshift |

Amended

Figure 1A - 4

| Number | | | | Nucleotide Base | | | | Gene | Nature of mutation |
|---|---|---|---|---|---|---|---|---|---|
| J | LKR | MTR | P12 | J | LKR | MTR | P12 | | |
| 591871 | 591173 | 590826 | 591288 | T | T | Δ T | Δ T | hypothetical protein YP_279264.1 | Frameshift |
| 608132 | 607408 | 607065 | 607536 | T | T | Δ T | Δ T | hypothetical protein YP_279278.1 | Frameshift |
| 613911 | 613182 | 612838 | 613309 | A | A | Δ A | Δ A | Intergenic | |
| 615799 | 615068 | 614722 | 615194 | T | T | Δ T | Δ T | hypothetical protein YP_279283.1 | Frameshift |
| 615804 | 615073 | 614726 | 615198 | T | T | Δ T | Δ T | hypothetical protein YP_279283.1 | Frameshift |
| 625870 | 625093 | 624770 | 625256 | - | - | ins T | ins T | Glutamine (Q) insertion into Putative P216 surface protein YP_279290.1 | In frame single codon insertion |
| 625871 | 625094 | 624771 | 625257 | - | - | ins T | ins T | | |
| 625872 | 625095 | 624772 | 625258 | - | - | ins G | ins G | | |
| 628031 | 627256 | 626935 | 627422 | T | T | Δ T | Δ T | putative P216 surface protein YP_279290.1 | Frameshift |
| 634595 | 633816 | 633492 | 633982 | A | A | Δ A | Δ A | Intergenic | |
| 683823 | 682998 | 682639 | 683159 | A | A | Δ A | Δ A | DNA gyrase subunit A YP_279326.1 | Frameshift |
| 699407 | 698575 | 698206 | 698737 | A | A | Δ A | Δ A | hypothetical protein YP_279337.1 | Frameshift |
| 699923 | 699090 | 698720 | 699252 | T | T | Δ T | Δ T | hypothetical protein YP_279338.1 | Frameshift |
| 733700 | 732825 | 732446 | 732988 | C | C | Δ C | Δ C | Intergenic | |
| 737657 | 736776 | 736391 | 736941 | T | T | Δ T | Δ T | hypothetical protein YP_279366.1 | Frameshift |
| 748454 | 747553 | 747173 | 747719 | A | A | Δ A | Δ A | Intergenic | |
| 768571 | 767650 | 767256 | 767824 | A | A | Δ A | Δ A | ribonuclease HII YP_279388.1 | Frameshift |
| 785221 | 784232 | 783880 | 784420 | A | A | Δ A | Δ A | inorganic pyrophosphatase YP_279400.1 | Frameshift |
| 810058 | 809042 | 808665 | 809219 | A | A | Δ A | Δ A | Intergenic | |
| 810061 | 809045 | 808667 | 809221 | A | A | Δ A | Δ A | Intergenic | |
| 817687 | 816667 | 816280 | 816841 | T | T | Δ T | Δ T | putative ABC transporter ATP-binding-Pr1 YP_279419.1 | Frameshift |
| 875082 | 873990 | 873584 | 874167 | T | T | Δ T | Δ T | putative adhesion like-protein P146 YP_279457.1 | Frameshift |
| 882753 | 881654 | 881253 | 881828 | T | T | Δ T | Δ T | Intergenic | |
| 883049 | 881950 | 881546 | 882123 | T | T | Δ T | Δ T | Intergenic | |
| 896830 | 895718 | 895303 | 895892 | A | A | Δ A | Δ A | putative inner membrane protein translocase component YidC YP_279468.1 | Frameshift |

Amended

Figure 1B - 1

| Mutation # | Nucleotide position (base pair) | | | | Nucleotide Base (positive strand) | | | | Translated Codon | | | | Amino Acid | | | | Gene [NCBI Ref Sequence] |
|---|---|---|---|---|---|---|---|---|---|---|---|---|---|---|---|---|---|
| | J | LKR | MTR | P12 | J | LKR | MTR | P12 | J | LKR | MTR | P12 | J | LKR | MTR | P12 | |
| 1 | 6060 | 6055 | 6051 | 6055 | G | G | A | A | TTG | TTG | TTA | TTA | Leu | Leu | Leu | Leu | Putative MgpA-like protein [YP_278810.1] |
| | | | | | | | | | | | | | No change | | | | |
| 2 | 10909 | 10898 | 10889 | 10900 | G | G | A | A | GCC | GCC | ACC | ACC | Ala | Ala | Thr | Thr | Hypothetical protein [YP_278814.1] |
| 3 | 96181 | 96082 | 96022 | 96106 | A | A | G | G | Intergenic | | | | Untranslated | | | | Intergenic sequence between amino acid permease [YP_278882.1] and NADH oxidase [YP_278883.1] |
| 4 | 118293 | 118165 | 118090 | 118184 | A | A | G | G | GAC | GAC | GGC | GGC | Asp | Asp | Gly | Gly | Hypothetical protein [YP_278896.1] |
| 5 | 123175 | 123040 | 122956 | 123057 | G | G | T | T | GTT | GTT | TTT | TTT | Val | Val | Phe | Phe | Putative outer membrane protein P95 [YP_278901.1] |
| 6 | 163911 | 163705 | 163605 | 163716 | G | G | A | A | TCC | TCC | TTC | TTC | Ser | Ser | Phe | Phe | Uracil-DNA glycosylase [YP_278929.1] |

Amended

Figure 1B - 2

| Mutation # | Nucleotide position (base pair) | | | | Nucleotide Base (positive strand) | | | | Translated Codon | | | | Amino Acid | | | | Gene [NCBI Ref Sequence] |
|---|---|---|---|---|---|---|---|---|---|---|---|---|---|---|---|---|---|
| | J | LKR | MTR | P12 | J | LKR | MTR | P12 | J | LKR | MTR | P12 | J | LKR | MTR | P12 | |
| 7 | 246307 | 246019 | 245861 | 246052 | G | G | T | T | GGC | GGC | TGC | TGC | Gly | Gly | Cys | Cys | Hypothetical protein [YP_279014.1] |
| 8 | 259905 | 259596 | 259427 | 259630 | G | G | A | A | STOP | STOP | STOP | STOP | No change | | | | myo-inositol catabolism protein [YP_279022.1] |
| 9 | 330948 | 330552 | 330348 | 330612 | A | A | G | G | AAT | AAT | AAC | AAC | Asn | Asn | Asn | Asn | DNA topoisomerase I [YP_279077.1] |
| 10 | 330998 | 330602 | 330398 | 330662 | A | A | G | G | TAT | TAT | CAT | CAT | Tyr | Tyr | His | His | DNA topoisomerase I [YP_279077.1] |
| 11 | 379103 | 378647 | 378432 | 378731 | C | C | G | G | Intergenic | | | | Untranslated | | | | Intergenic sequence between putative ISMHp1 transposase [YP_279110.1] and hyopthetical protein [YP_279111.1] |
| 12 | 385924 | 385463 | 385243 | 385547 | C | C | T | T | GAA | GAA | AAA | AAA | Glu | Glu | Lys | Lys | Hypothetical protein [YP_279117.1] |
| 13 | 411019 | 410537 | 410289 | 410618 | G | G | A | A | Truncated (pseudo) | | | | | | | | Putative transposase |

Amended

Figure 1B - 3

| Mutation # | Nucleotide position (base pair) | | | | Nucleotide Base (positive strand) | | | | Translated Codon | | | | Amino Acid | | | | Gene [NCBI Ref Sequence] |
|---|---|---|---|---|---|---|---|---|---|---|---|---|---|---|---|---|---|
| | J | LKR | MTR | P12 | J | LKR | MTR | P12 | J | LKR | MTR | P12 | J | LKR | MTR | P12 | |
| | | | | | | | | | | | | | | | | | truncated (pseudo) |
| 14 | 438867 | 438357 | 438081 | 438434 | G | G | A | A | GGA | GGA | GAA | GAA | Gly | Gly | Glu | Glu | Hypothetical protein [YP_279159.1] |
| 15 | 445620 | 445107 | 444821 | 445182 | C | C | A | A | CCC | CCC | CCA | CCA | Pro | Pro | Pro | Pro | Putative lipoprotein [YP_279163.1] |
| | | | | | | | | | | | | | No change | | | | |
| 16 | 446756 | 446242 | 445952 | 446317 | C | C | A | A | CTT | CTT | ATT | ATT | Leu | Leu | Ile | Ile | Putative ABC transporter permease protein [YP_279164.2] |
| 17 | 478690 | 478134 | 477852 | 478227 | G | G | A | A | Intergenic | | | | Untranslated | | | | Intergenic sequence between putative transposase [YP_279183.1] and hypothetical protein [YP_279186.1] |
| 18 | 495301 | 494704 | 494422 | 494807 | G | G | T | T | GGT | GGT | TGT | TGT | Gly | Gly | Cys | Cys | Nicotinate phosphoribosyltransferase [YP_279204.1] |

Amended

Figure 1B - 4

| Mutation # | Nucleotide position (base pair) | | | | Nucleotide Base (positive strand) | | | | Translated Codon | | | | Amino Acid | | | | Gene [NCBI Ref Sequence] |
|---|---|---|---|---|---|---|---|---|---|---|---|---|---|---|---|---|---|
| | J | LKR | MTR | P12 | J | LKR | MTR | P12 | J | LKR | MTR | P12 | J | LKR | MTR | P12 | |
| 19 | 538653 | 538003 | 537692 | 538116 | G | G | A | A | GCT | GCT | GTT | GTT | Ala | Ala | Val | Val | Hypothetical protein [YP_279238.1] |
| 20 | 539150 | 538495 | 538185 | 538608 | A | A | C | C | Intergenic | | | | Untranslated | | | | Intergenic sequence between two hypothetical proteins [YP_279238.1] and [YP_279239.1] |
| 21 | 539587 | 538926 | 538615 | 539041 | T | T | C | C | Intergenic | | | | Untranslated | | | | Intergenic sequence between two hypothetical proteins [YP_279238.1] and [YP_279239.1] |
| 22 | 539601 | 538940 | 538629 | 539055 | G | G | C | C | Intergenic | | | | Untranslated | | | | Intergenic sequence between two hypothetical proteins [YP_279238.1] and [YP_279239.1] |

Amended

Figure 1B - 5

| Mutation # | Nucleotide position (base pair) | | | | Nucleotide Base (positive strand) | | | | Translated Codon | | | | Amino Acid | | | | Gene [NCBI Ref Sequence] |
|---|---|---|---|---|---|---|---|---|---|---|---|---|---|---|---|---|---|
| | J | LKR | MTR | P12 | J | LKR | MTR | P12 | J | LKR | MTR | P12 | J | LKR | MTR | P12 | |
| 23 | 550628 | 549965 | 549652 | 550083 | C | C | A | A | GGG | GGG | GTG | GTG | Gly | Gly | Val | Val | Hypothetical protein [YP_279240.1] |
| 24 | 554103 | 553440 | 553126 | 553557 | G | G | A | A | CCC | CCC | CTC | CTC | Pro | Pro | Leu | Leu | Hypothetical protein [YP_279241.1] |
| 25 | 555585 | 554921 | 554606 | 555039 | G | G | T | T | ACT | ACT | AAT | AAT | Thr | Thr | Asn | Asn | Hypothetical protein [YP_279241.1] |
| 26 | 583967 | 583282 | 582945 | 583395 | G | G | T | T | GGG | GGG | GTG | GTG | Gly | Gly | Val | Val | Hypothetical protein [YP_279257.1] |
| 27 | 599805 | 599096 | 598745 | 599214 | C | C | A | A | GAT | GAT | TAT | TAT | Asp | Asp | Tyr | Tyr | Hypothetical protein [YP_279271.1] |
| 28 | 615445 | 614715 | 614370 | 614840 | C | C | A | A | AGT | AGT | ATT | ATT | Ser | Ser | Ile | Ile | Hypothetical protein [YP_279283.1] |
| 29 | 743961 | 743064 | 742685 | 743229 | G | G | A | A | GCA | GCA | GTA | GTA | Ala | Ala | Val | Val | Putative PTS system N-acetylglucosamine-specific II ABC component [YP_279370.1] |
| 30 | 848512 | 847456 | 847061 | 847629 | C | C | G | G | ATG | ATG | ATC | ATC | Met | Met | Ile | Ile | Leucyl-tRNA synthetase YP_279441.1 |
| 31 | 881437 | 880340 | 879938 | 880514 | A | A | G | G | Untranslated | | | | Untranslated | | | | 16S ribosomal |

Amended

Figure 1B - 6

| Mutation # | Nucleotide position (base pair) | | | | Nucleotide Base (positive strand) | | | | Translated Codon | | | | Amino Acid | | | | Gene [NCBI Ref Sequence] |
|---|---|---|---|---|---|---|---|---|---|---|---|---|---|---|---|---|---|
| | J | LKR | MTR | P12 | J | LKR | MTR | P12 | J | LKR | MTR | P12 | J | LKR | MTR | P12 | |
| | | | | | | | | | | | | | | | | | RNA MHJ_0709 |

J - Published whole genome sequence of *M. hyopneumoniae* J strain (NC_007295.1; SEQ ID NO:5)
LKR - Parental strain of Vaxsafe® MHP
MTR - Master Seed Level (3 passages from Master seed) of Vaxsafe® MHP
P12 - Late passage (12 passages from Working Seed) of Vaxsafe® MHP Amended

Figure 1C - 1

| Mutation # | Gene [NCBI Reference Sequence] | Amino acid (aa) change [residue number] | Amino acid characteristic original aa | Amino acid characteristic mutated aa |
|---|---|---|---|---|
| 1 | Putative MgpA-like protein [YP_278810.1] | L[249]L | Aliphatic hydrophobic neutral | Aliphatic hydrophobic neutral |
| 2 | Hypothetical protein [YP_278814.1] | A[574]T | Aliphatic hydrophobic neutral | Polar hydrophilic neutral |
| 3 | Intergenic sequence between amino acid permease [YP_278882.1] and NADH oxidase [YP_278883.1] | | | |
| 4 | Hypothetical protein [YP_278896.1] | D[299]G | Polar hydrophilic charged (-) | Aliphatic neutral |
| 5 | Putative outer membrane protein P95 [YP_278901.1] | V[37]F | Aliphatic hydrophobic neutral | Aromatic hydrophobic neutral |
| 6 | Uracil-DNA glycosylase [YP_278929.1] | S[131]F | Polar hydrophilic neutral | Aromatic hydrophobic neutral |
| 7 | Hypothetical protein [YP_279014.1] | G[1884]C | Aliphatic neutral | Polar hydrophobic neutral |
| 8 | myo-inositol catabolism protein iolC [YP_279022.1] | Stop Stop | | |
| 9 | DNA topoisomerase I [YP_279077.1] | N[39]N | Polar hydrophilic neutral | Polar hydrophilic neutral |
| 10 | DNA topoisomerase I [YP_279077.1] | Y[23]H | Aromatic polar hydrophobic | Aromatic polar hydrophilic charge (+) |
| 11 | Intergenic sequence between | | | |

Amended

Figure 1C - 2

| Mutation # | Gene [NCBI Reference Sequence] | Amino acid (aa) change [residue number] | Amino acid characteristic | Amino acid characteristic |
|---|---|---|---|---|
| | | | original aa | mutated aa |
| | putative ISMHp1 transposase [YP_279110.1] and hyopthetical protein [YP_279111.1] | | | |
| 12 | Hypothetical protein [YP_279117.1] | E[18]K | Polar hydrophilic charged (-) | Polar hydrophilic charged (+) |
| 13 | Putative transposase truncated (pseudo) | | | |
| 14 | Hypothetical protein [YP_279159.1] | G[73]E | Aliphatic neutral | Polar hydrophilic charged (-) |
| 15 | Putative lipoprotein [YP_279163.1] | P[50]P | Hydrophobic neutral | Hydrophobic neutral |
| 16 | Putative ABC transporter permease protein [YP_279164.2] | L[114]I | Aliphatic hydrophobic neutral | Aliphatic hydrophobic neutral |
| 17 | Intergenic sequence between putative transposase [YP_279183.1] and hypothetical protein [YP_279186.1] | | | |
| 18 | Nicotinate phosphoribosyltransferase [YP_279204.1] | G[90]C | Aliphatic neutral | Polar hydrophobic neutral |
| 19 | Hypothetical protein [YP_279238.1] | A[128]V | Aliphatic hydrophobic neutral | Aliphatic hydrophobic neutral |
| 20 | Intergenic sequence between two hypothetical proteins [YP_279238.1] and [YP_279239.1] | | | |

Amended

Figure 1C - 3

| Mutation # | Gene [NCBI Reference Sequence] | Amino acid (aa) change [residue number] | Amino acid characteristic | Amino acid characteristic |
|---|---|---|---|---|
| | | | original aa | mutated aa |
| 21 | Intergenic sequence between two hypothetical proteins [YP_279238.1] and [YP_279239.1] | | | |
| 22 | Intergenic sequence between two hypothetical proteins [YP_279238.1] and [YP_279239.1] | | | |
| 23 | Hypothetical protein [YP_279240.1] | G[204]V | Aliphatic neutral | Aliphatic hydrophobic neutral |
| 24 | Hypothetical protein [YP_279241.1] | P[650]L | Hydrophobic neutral | Aliphatic hydrophobic neutral |
| 25 | Hypothetical protein [YP_279241.1] | T[156]N | Polar hydrophilic neutral | Polar hydrophilic neutral |
| 26 | Hypothetical protein [YP_279257.1] | G584V | Aliphatic neutral | Aliphatic hydrophobic neutral |
| 27 | Hypothetical protein [YP_279271.1] | D[230]Y | Polar hydrophilic charged (-) | Aromatic polar hydrophobic |
| 28 | Hypothetical protein [YP_279283.1] | S[389]I | Polar hydrophilic neutral | Aliphatic hydrophobic neutral |
| 29 | Putative PTS system N-acetylglucosamine-specific II ABC component [YP_279370.1] | A[159]V | Aliphatic hydrophobic neutral | aliphatic hydrophobic neutral |
| 30 | Leucyl-tRNA synthetase YP_279441.1 | M[440]I | Hydrophobic neutral | Aliphatic hydrophobic neutral |

Amended

Figure 1C - 4

| Mutation # | Gene [NCBI Reference Sequence] | Amino acid (aa) change [residue number] | Amino acid characteristic | Amino acid characteristic |
|---|---|---|---|---|
| | | | original aa | mutated aa |
| 31 | 16S ribosomal RNA MHJ_0709 | | | |

J - Published whole genome sequence of *M. hyopneumoniae* J strain (NC_007295.1; SEQ ID NO:5)
LKR - Parental strain of Vaxsafe® MHP
MTR - Master Seed Level (3 passages from Master seed) of Vaxsafe® MHP
P12 - Late passage (12 passages from Working Seed) of Vaxsafe® MHP Amended Figure 4
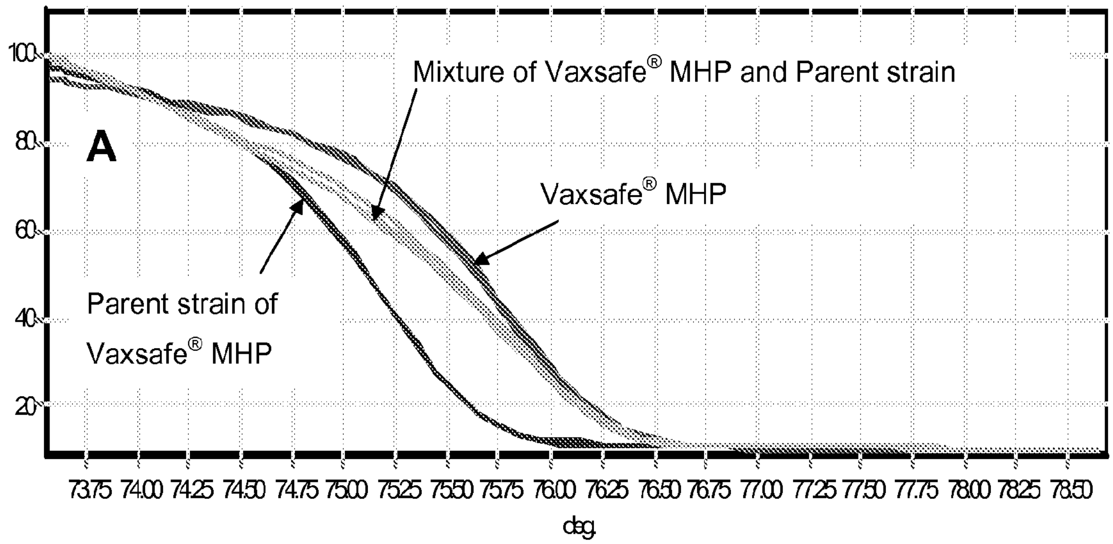
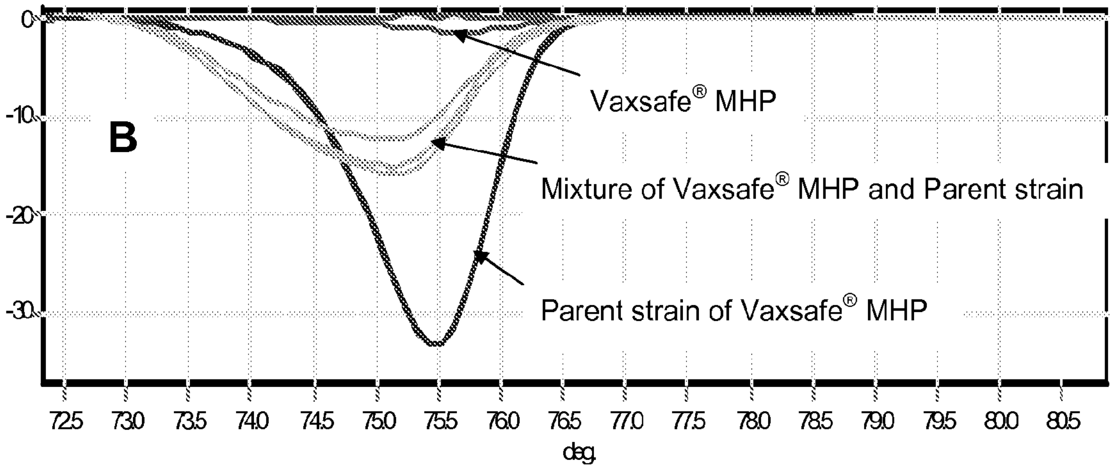

METHODS RELATING TO AN ATTENUATED MYCOPLASMA

FIELD

The present invention relates to uses for attenuated *Mycoplasma hyopneumoniae*, such as in methods for diagnosing the presence of attenuated *Mycoplasma* in a sample and for selecting for attenuated *Mycoplasma*.

BACKGROUND

*Mycoplasma hyopneumoniae* is the etiological agent of swine Mycoplasmal pneumonia (also called enzootic pneumonia (EP)). It is one of the most common and economically significant respiratory diseases affecting swine production worldwide. The disease is associated with secondary infections, high-morbidity and low-mortality rates, low feed conversion and can be attributed to global economic losses estimated at about $1 billion per year.

In EP, *Mycoplasma hyopneumoniae* bacteria attach to the cilia of epithelial cells in the lungs of swine destroying healthy normal cilia allowing for opportunistic organisms to establish themselves into the respiratory tissue causing disease. Once established, *M. hyopneumoniae* causes lesions in the lungs of pigs.

The disease is highly contagious and transmission is usually through direct contact with infected respiratory tract secretions, for example droplets ejected from the snout or mouth on sneezing or coughing.

Several vaccines against *M. hyopneumoniae* currently exist. Most current vaccines are provided by about 10 companies with 22 vaccine brands registered as either single or bi/multivalent. All are killed or inactivated *M. hyopneumoniae* preparations.

Examples of whole cell inactivated *M. hyopneumoniae* vaccines include RESPISURE™ and STELLAMUNE™ (Pfizer), SUVAXYN *M. HYO*™ (Fort Dodge), HYORESP™ (Merial), M+PAC™ (Schering-Plough) and PORCILIS™ (Intervet).

While some vaccines can reduce the severity of EP, none of the available whole cell killed or inactivated vaccines provide full protection from *M. hyopneumoniae* infection.

Our co-pending application, published as WO2010/132932, describes a live attenuated *M. hyopneumoniae* strain which is temperature sensitive. This strain is designated ts-19 and was deposited under the Budapest Treaty at the National Measurements Institute as NM 04/41259 on 13 May 2004. This strain, when incorporated into a vaccine, is able to confer protective immunity against *M. hyopneumoniae* in vaccinated pigs.

SUMMARY

A first aspect provides a method for identifying an attenuated *Mycoplasma* bacterium, the method comprising assaying *Mycoplasma* bacteria for presence of a mutation in at least one gene encoding a protein listed in Table 1 or in a nucleic acid molecule listed in any one or more of Tables 2 to 5, wherein the presence of the mutation indicates that the *Mycoplasma* is attenuated.

Attenuated vaccines are generally advantageous because they present all the relevant immunogenic determinants of an infectious agent in its natural form to the host's immune system and the need for relatively small amounts of the immunising agent due to the ability of the agent to multiply in the vaccinated host. Methods for attenuating include passaging a virulent strain multiple times or exposure to irradiation or chemicals. It is assumed that these methods introduce mutations in the genome which render the microorganism less virulent but still capable of replication.

Disadvantages of these approaches are that they introduce random mutations that are not characterised at the molecular level. Also methods for selecting for attenuation, such as by selecting for associated temperature sensitivity are often time consuming, produce false results as a temperature sensitive strain may not be attenuated and an attenuated strain need not be temperature sensitive, and require a great deal of trial and error. Additionally the attenuated strain may undergo further mutation and revert to virulence. An alternative strategy would be to generate non-reversible genetically defined attenuated *Mycoplasma*. However to date the genes affected by attenuation of *Mycoplasma* have not been identified. The present invention identifies mutations in an attenuated *Mycoplasma* as compared to its parent strain and utilises this knowledge to determine which genes should be mutated to provide an attenuated *Mycoplasma*.

The method of the first aspect allows selection for an attenuated *Mycoplasma* strain and to identify if an attenuated strain has returned to virulence.

A second aspect provides a method for generating an attenuated *Mycoplasma*, the method comprising subjecting an initial population of *Mycoplasma* bacteria to attenuating conditions, thereby producing a putatively attenuated bacterial population and assaying individual clones of the putatively attenuated bacterial population for presence of a mutation in at least one gene encoding a protein listed in Table 1 or in a nucleic acid molecule listed in any one or more of Tables 2 to 5 wherein the presence of the mutation indicates that the *Mycoplasma* is attenuated.

A third aspect provides an attenuated *Mycoplasma* bacteria selected by the method of the first aspect or generated by the method of the second aspect.

A fourth aspect provides an immunogenic composition comprising the attenuated *Mycoplasma* bacteria of the third aspect.

A fifth aspect provides a *Mycoplasma* vaccine comprising the immunogenic composition of the fourth aspect.

A sixth aspect provides a method of inducing protective immunity against a disease caused by a *Mycoplasma* in a subject, the method comprising administering to the subject a protective amount of the attenuated *Mycoplasma* of the third aspect, the immunogenic composition of the fourth aspect or the vaccine of the fifth aspect.

An alternative aspect provides the attenuated *Mycoplasma* of the third aspect, the immunogenic composition of the fourth aspect or the vaccine of the fifth aspect for eliciting protective immunity against a disease cause by *Mycoplasma*.

A further alternative aspect provides for use of the attenuated *Mycoplasma* of the third aspect, the immunogenic composition of the fourth aspect or the vaccine of the fifth aspect in the manufacture of a medicament for preventing a disease caused by *Mycoplasma*.

The inventors determined the nucleic acid sequence of the attenuated *Mycoplasma hyopneumoniae* strain (ts-19) deposited with the National Measurements Institute under accession number NM04/41259, and the sequence of the virulent strain from which the attenuated strain was derived by NTG mutation (*Mycoplasma hyopneumoniae* isolate LKR, Lloyd & Etheridge (1981) J. Comp. Path. 91:77-83). Using analysis of the aligned sequences together with their knowledge in the field, the inventors were able to identify certain mutations they believe to be associated with attenuation. The inventors consider that these mutations are markers for attenuation in

*Mycoplasma hyopneumoniae* and in other *Mycoplasma* and can be used to select for attenuated *Mycoplasma* strains. This is particularly useful when attenuation conditions used to generate an attenuated *Mycoplasma* cause random mutagenesis. Selection for the mutations provides a simple method of determining if a strain of *Mycoplasma* is attenuated and therefore suitable for formulation into a vaccine.

A seventh aspect provides a method for determining if an animal is infected with an attenuated or virulent strain of *Mycoplasma*, the method comprising assaying a sample comprising a *Mycoplasma* from an animal for presence of a mutation in at least one gene encoding a protein listed in Table 1 or in a nucleic acid molecule listed in any one or more of Tables 2 to 5, wherein the absence of the mutation indicates that the animal is infected with virulent *Mycoplasma*.

An eighth aspect provides a method for distinguishing animals vaccinated with an attenuated *Mycoplasma* strain from those infected with *Mycoplasma*, the method comprising assaying a sample comprising a *Mycoplasma* for presence of a mutation in at least one gene encoding a protein listed in Table 1 or in a nucleic acid molecule listed in any one or more of Tables 2 to 5 wherein the presence of the mutation in the sample indicates that animal from which the sample was taken has been vaccinated with an attenuated *Mycoplasma* vaccine.

*Mycoplasma hyopneumoniae* is a highly contagious and chronic disease causing enzootic pneumonia in pigs. This disease is endemic world wide. The methods of the sevenths and eighth aspects allow differentiation of pigs which have been vaccinated with an attenuated strain from those that are infected or whose vaccine strain has reverted to virulence.

A ninth aspect provides a kit comprising primers or probes specific for a mutation in one or more genes encoding a protein listed in Table 1 or in a nucleic acid molecule listed in any one or more of Tables 2 to 5.

A tenth aspect provides a kit comprising primers or probes specific for at least one mutation shown in FIG. 1.

The kits of the ninth and tenth aspects may be used in the methods of the first, seventh or eighth aspects.

DETAILED DESCRIPTION

*M. hyopneumoniae* strain "LKR" was originally isolated from an abattoir specimen (Lloyd and Etheridge 1981, J of Comp Path 91:77-83). The organism was reisolated from experimentally infected pigs prior to being passaged about 10 times in acellular medium to reach clonal isolation (CSIRO, Victoria). The clone was then submitted to the University of Adelaide *Mycoplasma* collection, South Australia. The LKR isolate was then obtained by the University of Melbourne, Department of Veterinary Science (*Mycoplasma* Group), where it underwent 3 in vitro passages in modified Friss broth, for storage. The stored vials were designated "LKR P3 29/5/97". This clone represents the parental strain.

LKR P3 29/5/97 was in vitro passaged and subjected to NTG mutagenesis (200 mg/mL) using a method described previously (Nonamura and Imada (1982) Avian Diseases 26:763-775). A temperature sensitive clone ("ts-19") was selected from an agar plate and cultured in 3 mL modified Friss broth. Passage number for this clone was designated "P0" and had subsequently undergone a further four in vitro passages at 1:4 v/v dilution per passage in modified Friss broth. The final passage level was designated "LKR ts-19 P4 MS".

LKR ts-19 P4 MS underwent a number of in vitro dilution passages in Modified Friss broth to reach a dilution of $3.2\times10^{-21}$. The final mutant clone was designated "LKR ts-19 $3.2\times10^{-21}$".

LKR ts-19 $3.2\times10^{-21}$ was freeze dried and submitted to Australian Government Analytical Laboratories (Budapest Treaty on the International recognition of the deposit of organisms for the purposes of patent procedure) under the accession number NM04/41259.

*Mycoplasmas* have a highly reduced genome size which reflects their limited biosynthetic abilities and their parasitic like dependence on their host. In light of the limited redundancy in their genomes, NTG mutagenesis of a particular component of a pathway may have a significant effect on the survival of a *Mycoplasma* cell. NTG mutagenesis results in random mutations (nucleotide transitions, transversions, deletions or insertions) within the genome. This would result in a population of variant genomes each containing either one or more mutations. Presumably many of the variant genomes would not survive due to a critical gene or genes being rendered dysfunctional. If the mutations do not incur a detrimental effect on the organisms ability to grow then those surviving variant organisms can undergo further selection (e.g. temperature selection). In the development of ts-19, the selection was based on the ability of the variant strain to grow to high titre at a temperature of 33° C. and the reduced ability to grow at 39.5° C. Based on whole genome sequence comparison between *Mycoplasma hyopneumoniae* vaccine strain ts-19 and that of the parent strain (LKR), a number of mutations (nucleotide changes) have been identified within the genome of ts-19. These mutations included nucleotide substitutions (transitions and transversions), as well as deletions and insertions.

The mutations were located around the entire genome and include a range of expressed genes as well as hypothetical proteins and non-coding sequences. Table 1 lists the known genes that have been mutated by base substitutions, deletions or insertions. The genes have been categorized according to their main function.

Table 2 shows silent mutations identified in genes and in non-coding regions of ts-19. Table 3 shows deletions identified in non-coding regions of ts-19. Table 4 shows mutations identified in hypothetical genes of ts-19. Table 5 shows deletions identified in hypothetical genes of ts-19.

The exact nature of the specific differences between *M. hyo* J strain, *M. hyo* LKR strain, and the ts-19 attenuated strain (master and after 12 in vitro passages) are shown in FIG. 1.

It is postulated that temperature sensitivity and attenuation of an organism results from either a single or multiple mutations that act individually or in concert to produce the phenotypic characteristics.

Persons skilled in the art would readily appreciate how to identify if a *M. hyo* strain contained a mutation in one of the genes listed in Table 1 by determining if there is a difference between the reference sequence provide (e.g. YP_278901.1) and the sequence of the attenuated strain ts-19, as deposited as NM04/41259.

In one embodiment the attenuated strain comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34 or all of the mutations listed in Table 1, alone or in combination with at least one mutation listed in Table 2, 3, 4 or 5.

In one embodiment the attenuated strain comprises a mutation in one or each of the virulence factors, and/or one or each of the genes involved in carbohydrate metabolism, and/or the gene involved in phospholipid metabolism, and/or the gene involved in co-factor metabolism, and/or one or each of the genes involved in transcription or translation, and/or one or each of the genes involved in membrane transport, and/or one or each of the genes involved in DNA replication, repair or metabolism and/or the transposase gene listed in Table 1.

In one embodiment the attenuated strain comprises a mutation in each of the virulence factors.

Mutations found within the P95, P69, P216, P146 genes as well as lipoprotein genes are most likely to have an effect on attenuation as these genes have been described as being associated with virulence (Ferreira and de Castro et al., (2007). Genetic and Molecular Biology 30: p 245-255).

In another embodiment the attenuated strain comprises at least 1, 2, 3, 4, 5, 6, 7, 8, 9, 10 or all of the mutations listed in Table 2, alone or in combination with at least one mutation listed in Table 1, 3, 4 or 5.

In another embodiment the attenuated strain comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44 or all of the mutations listed in Table 3, alone or in combination with at least one mutation listed in Table 1, 2, 4 or 5.

In another embodiment the attenuated strain comprises at least 1, 2, 3, 4, 5, 6, 7, 8, 9, 10 or all of the mutations listed in Table 4, alone or in combination with at least one mutation listed in Table 1, 2, 4 or 5.

In another embodiment the attenuated strain comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or all of the mutations listed in Table 5, alone or in combination with at least one mutation listed in Table 1, 2, 3 or 4.

TABLE 1

Attenuating Mutations within genes of *M. hyopneumoniae* vaccine strain ts-19.

| | |
|---|---|
| Virulence factors: | |
| Putative outer membrane protein P95 | YP_278901.1 |
| Putative lipoprotein (MHJ_0213) | YP_279015.1 |
| Putative lipoprotein (MHJ_0362) | YP_279161.1 |
| Putative P216 surface protein | YP_279290.1 |
| Putative adhesion like-protein P146 | YP_279457.1 |
| Carbohydrate Metabolism: | |
| Triosephosphate isomerase | YP_278904.1 |
| Transketolase | YP_279223.1 |
| Putative PTS system N-acetylglucosamine-specific II ABC Component | YP_279370.1 |
| Phospholipid Metabolism: | |
| CDP-diacylglycerol-glycerol-3-phosphate-3-phosphatidyal transferase | YP_279075.1 |
| Co-factors Metabolism: | |
| Nicotinate phosphoribosyltransferase | YP_279204.1 |
| Transcription/translation: | |
| GidA gene [tRNA uridine 5-carboxymethylaminomethyl modification enzyme | YP_278808.1 |
| 50S Ribosomal protein L3 | YP_278992.1 |
| Leucyl-tRNA synthetase | YP_279441.1 |
| Isoleucyl tRNA synthetase | YP_278833.1 |
| Membrane Transport: | |
| Putative ABC transporter permease protein | YP_279164.2 |
| Putative ABC transporter ATP binding | YP_278823.1 |
| Putative chromate transport protein | YP_278943.1 |
| Putative ABC transporter ATP binding and permease protein | YP_278958.1 |
| Putative inner membrane protein translocase component YidC | YP_279468.1 |
| Putative ABC transport system permease protein p69-like | YP_279157.1 |

TABLE 1-continued

Attenuating Mutations within genes of *M. hyopneumoniae* vaccine strain ts-19.

| | |
|---|---|
| Putative ABC transporter permease protein | YP_279176.1 |
| Putative ABC transporter ATP-binding-Pr1 | YP_279419.1 |
| DNA replication/repair/metabolism | |
| DNA topoisomerase I | YP_279077.1 |
| Uracil-DNA glycosylase | YP_278929.1 |
| GTPase ObgE | YP_278842.1 |
| DNA polymerase IV | YP_278846.1 |
| Ribonucleotide-disulphate reductase subunit alpha | YP_279017.1 |
| Thymidylate kinase | YP_279053.1 |
| DNA polymerase III subunit delta | YP_279054.1 |
| DNA ligase | YP_279060.1 |
| DNA gyrase subunit A | YP_279326.1 |
| ribonuclease HII | YP_279388.1 |
| Inorganic pyrophosphatase | YP_279400.1 |
| Excinuclease ABC subunit C | YP_278867.1 |
| Transposase | |
| putative ISMHp1 transposase | YP_279110.1 |

YP_number indicates NCBI Reference Sequence

TABLE 2

Attenuating Mutations within *M. hyopneumoniae* vaccine strain ts-19 which are silent or in non-coding region.

| Mutation # | Silent mutations in genes and mutations in non-coding regions [NCBI Reference Sequence] |
|---|---|
| 1 | Putative MgpA-like protein [YP_278810.1] |
| 2 | Intergenic sequence between amino acid permease [YP_278882.1] and NADH oxidase [YP_278883.1] |
| 3 | myo-inositol catabolism protein [YP_279022.1] |
| 4 | Intergenic sequence between putative ISMHp1 transposase [YP_279110.1] and hyopthetical protein [YP_279111.1] |
| 5 | Putative transposase truncated (pseudo) |
| 6 | Putative lipoprotein [YP_279163.1] |
| 7 | Intergenic sequence between putative transposase [YP_279183.1] and hypothetical protein [YP_279186.1] |
| 8 | Intergenic sequence between two hypothetical proteins [YP_279238.1] and [YP_279239.1] |
| 9 | Intergenic sequence between two hypothetical proteins [YP_279238.1] and [YP_279239.1] |
| 10 | Intergenic sequence between two hypothetical proteins [YP_279238.1] and [YP_279239.1] |
| 11 | 16S ribosomal RNA MHJ_0709 |

TABLE 3

Deletion mutations in non-coding regions of the *M. hyopneumoniae* vaccine strain ts-19.

| Deletion # | Nucleotide position | Genomic region |
|---|---|---|
| 1 | 17111 | Intergenic |
| 2 | 48804 | Intergenic |
| 3 | 59468 | Intergenic |
| 4 | 66236 | Intergenic |
| 5 | 89570 | Intergenic |
| 6 | 94587 | Intergenic |
| 7 | 94589 | Intergenic |
| 8 | 104212 | Intergenic |
| 9 | 104213 | Intergenic |
| 10 | 117188 | Intergenic |
| 11 | 120729 | Intergenic |
| 12 | 133537 | Intergenic |
| 13 | 143156 | Intergenic |
| 14 | 143243 | Intergenic |
| 15 | 147100 | Intergenic |
| 16 | 153282 | Intergenic |
| 17 | 170050 | Intergenic |
| 18 | 187078 | Intergenic |

TABLE 3-continued

Deletion mutations in non-coding regions of the *M. hyopneumoniae* vaccine strain ts-19.

| Deletion # | Nucleotide position | Genomic region |
|---|---|---|
| 19 | 187103 | Intergenic |
| 20 | 213969 | Intergenic |
| 21 | 235066 | Intergenic |
| 22 | 246360 | Intergenic |
| 23 | 392955 | Intergenic |
| 24 | 409835 | Intergenic |
| 25 | 425552 | Intergenic |
| 26 | 425563 | Intergenic |
| 27 | 430879 | Intergenic |
| 28 | 430898 | Intergenic |
| 29 | 476785 | Intergenic |
| 30 | 476786 | Intergenic |
| 31 | 478329 | Intergenic |
| 32 | 490917 | Intergenic |
| 33 | 501705 | Intergenic |
| 34 | 523821 | Intergenic |
| 35 | 538279 | Intergenic |
| 36 | 563258 | Intergenic |
| 37 | 585116 | Intergenic |
| 38 | 612838 | Intergenic |
| 39 | 633492 | Intergenic |
| 40 | 732446 | Intergenic |
| 41 | 747173 | Intergenic |
| 42 | 808665 | Intergenic |
| 43 | 808667 | Intergenic |
| 44 | 881253 | Intergenic |
| 45 | 881546 | Intergenic |

TABLE 4

Mutations within hypothetical genes of the *M. hyopneumoniae* vaccine strain ts-19.

| Mutation # | Gene [NCBI Reference Sequence] |
|---|---|
| 1 | Hypothetical protein [YP_278814.1] |
| 2 | Hypothetical protein [YP_278896.1] |
| 3 | Hypothetical protein [YP_279014.1] |
| 4 | Hypothetical protein [YP_279117.1] |
| 5 | Hypothetical protein [YP_279159.1] |
| 6** | Hypothetical protein [YP_279238.1] |
| 7 | Hypothetical protein [YP_279240.1] |
| 8** | Hypothetical protein [YP_279241.1] |
| 9 | Hypothetical protein [YP_279257.1] |
| 10 | Hypothetical protein [YP_279271.1] |
| 11 | Hypothetical protein [YP_279283.1] |

**These hypothetical proteins have been described to be variable antigens (Ferreira and de Castro, (2007) supra.

TABLE 5

Deletions within hypothetical genes of the *M. hyopneumoniae* vaccine strain ts-19.

| Deletion # | Hypothetical Genes |
|---|---|
| 1 | Hypothetical protein YP_278812.1 |
| 2 | Hypothetical protein YP_278865.1 |
| 3 | Hypothetical protein YP_278873.1 |
| 4 | Hypothetical protein YP_278896.1 |
| 5 | Hypothetical protein YP_278896.1 |
| 6 | Hypothetical protein YP_278906.1 |
| 7 | Hypothetical protein YP_278917.1 |
| 8 | Hypothetical protein YP_278919.1 |
| 9 | Hypothetical protein YP_278948.1 |
| 10 | Hypothetical protein YP_278995.1 |
| 11 | Hypothetical protein YP_279003.1 |
| 12 | Hypothetical protein YP_279009.1 |
| 13 | Hypothetical protein YP_279032.2 |
| 14 | Hypothetical protein YP_279046.1 |
| 15 | Hypothetical protein YP_279121.1 |

TABLE 5-continued

Deletions within hypothetical genes of the *M. hyopneumoniae* vaccine strain ts-19.

| Deletion # | Hypothetical Genes |
|---|---|
| 16 | Hypothetical protein YP_279136.1 |
| 17 | Hypothetical protein YP_279138.1 |
| 18 | Hypothetical protein YP_279182.1 |
| 19 | Hypothetical protein YP_279196.1 |
| 20 | Hypothetical protein YP_279196.1 |
| 21 | Hypothetical protein YP_279217.1 |
| 22 | Hypothetical protein YP_279235.1 |
| 23 | Hypothetical protein YP_279242.1 |
| 24 | Hypothetical protein YP_279247.1 |
| 25 | Hypothetical protein YP_279262.1 |
| 26 | Hypothetical protein YP_279264.1 |
| 27 | Hypothetical protein YP_279278.1 |
| 28 | Hypothetical protein YP_279283.1 |
| 29 | Hypothetical protein YP_279283.1 |
| 30 | Hypothetical protein YP_279337.1 |
| 31 | Hypothetical protein YP_279338.1 |
| 32 | Hypothetical protein YP_279366.1 |

DETAILED DESCRIPTION

The present invention is based on the determination of the nucleic acid sequence of a temperature sensitive attenuated *M. hyo* strain (ts-19) and its parent strain. Alignment of these strains and others has allowed the location and nature of mutations in the attenuated strain to be identified.

Temperature sensitive mutations fall into general classes: those generating thermolabile proteins; and those generating defects in protein synthesis, folding or assembly. In the case of the thermolabile proteins, the is mutants of a gene may be expressed at a higher level at the permissive temperature (33° C. for ts-19) and at a lower level at the non-permissive temperature (39.5° C. for ts-19).

As used herein, the term “mutation” refers to any detectable change in genetic material, e.g. DNA, RNA, cDNA or any process, mechanism or result of such a change. Such mutations may be point mutations (i.e., mutations in which one or more bases within the nucleic acid sequence have been replaced by a different base), insertion mutations (i.e, mutations in which the total length of the nucleic acid molecule or gene has been increased by the insertion of one or more bases), deletion mutations (mutations in which the total length of the nucleic acid molecule or gene has been decreased by removal of one or more bases) and inversion mutations (mutations in which a region of two or more bases has been rotated 180 degrees), or combinations of these.

A mutation in an intergenic region refers to a mutation located in a non-coding region of the nucleic acid molecule.

Genes comprising a deletion of less than a total codon will produce a frameshift mutation. This will result in a gene product that will be composed of amino acids that have no or little resemblance to the original (native) protein. Therefore, the protein will be dysfunctional. This will impact the role of that protein as well as possibly the stability of that protein because it will no longer be able to fold or assemble correctly. Hence the expression level for that protein will be reduced or eliminated compared to the wild type.

A deletion may result in a premature termination of expression of the gene product. Once again, the function and the stability of that protein will be affected. Further to this, the truncated mRNA transcript may be unstable and readily degraded. Hence the expression level of the mutated protein will be reduced or eliminated compared to the wild type.

The attenuated ts-19 strain comprises numerous deletions that affect surface proteins such as the outer membrane protein P95, P216, P146, P69 and lipoproteins. Membrane transport proteins are also affected by deletion mutations which will render these gene products dysfunctional. Hence if you compared the expression of these genes with the parent strain LKR, we would expect to see a marked difference in the expression levels of these proteins.

A mutation caused by a single base substitution that results in an in-frame amino acid change may alter the folding or assembly of that protein and hence while it may be synthesized; it may not function in a correct manner. Such a protein may also affect the expression of numerous other genes that may be under the control or effect of the mutated protein.

In one embodiment the presence of a mutation in at least one gene encoding a protein listed in Table 1 is detected by assaying for a change in expression of at least one protein. In one embodiment the change in expression is a reduction or absence of expression. Persons skilled in the art can readily appreciate methods for determining if the expression of a protein is changed or reduced, for example by quantitative antibody-based methods such as Western blotting, radioimmunoassay (RIAs) and enzyme linked immunosorbant assays (ELISAs) in which an antibody is used which detects and binds to the protein of interest. In addition since mRNA levels generally reflect the quantity of the protein encoded therefrom, quantitative nucleic acid methods may also be used to determine whether the *Mycoplasma* exhibits reduced or absence of expression of one or more proteins. For example quantitative reverse transcriptase/polymerase chain reaction (RT-PCR) methods may be used to measure the quantity of mRNA corresponding to a particular protein of interest. Numerous quantitative nucleic acid based methods are well known in the art. Also qualitative nucleic acid based methods (e.g. Northern Blot analysis) are well known in the art.

In one embodiment, as ts-19 comprises a mutated form of leucyl-tRNA synthetase and a deleted form of isoleucyl tRNA synthetase, which are both involved in protein synthesis, total protein synthesis may be altered in attenuated *Mycoplasma* compared to wild type *Mycoplasma*. Accordingly in one embodiment the method comprises assaying *Mycoplasma* bacteria for total protein synthesis.

With regard to "reduction in expression" the reduction compared to wild type may be at least about 5% compared to wild type. In other embodiments the reduction in expression is at least about 10%, 15%, 20%, 25%, 30%, 35%, 40%, 45%, 50%, 55%, 60%, 65%, 70%, 75%, 80%, 85%, 95% or 99%. In another embodiment the bacteria exhibits no expression of a protein expressed in the wild type bacteria and hence the percentage reduction in expression in 100%.

In one embodiment the presence of a mutation in at least one gene encoding a protein listed in Table 1 or in a nucleic acid molecule listed in any one or more of Tables 2 to 5 is detected by assaying at a genetic level. i.e. assaying nucleic acid. Such an assay may be a PCR assay.

Suitable types of PCR assay include conventional PCR, multiplex PCR, quantitative PCR (qPCR), real time PCR (RT-PCR), fluorescent capillary electophoresis (CE), high resolution melting curve (HRM) analysis, melting temperature (Tm) analysis, variable number tandem repeat (VNTR) and mutli locus sequence typing (MLST) and single nucleotide primer extension assay.

Analysis of conventional PCR products will be straightforward to persons skilled in the art and may include techniques such as nucleotide sequence analysis, restriction fragment length polymorphism (RFLP) analysis, denaturing gradient gel electrophoresis (DGGE) and single-stranded conformational polymorphism (SSCP) analysis.

PCR amplifications may be performed by selecting PCR primers that flank the region of the mutation(s). Each PCR primer set will preferably produce only a single band (amplicon). The size of the amplicon may be of a size appropriate to the method of PCR based analysis.

While in part the invention relates to changes between the DNA sequence of a *M. hyo* wild type strain and its temperature sensitive attenuated strain, the finding that these mutations are linked to attenuation is applicable to all species of *Mycoplasma* comprising the same genes due to conservation of these proteins across *Mycoplasma* species.

The method of the first and second aspects and the attenuated *Mycoplasma* bacteria of third aspect may relate to any *Mycoplasma* species.

In one embodiment, the attenuated bacteria are derived from animal-pathogenic *Mycoplasma* bacteria. As used herein, the term "animal-pathogenic *Mycoplasma* bacterium" means a bacterium that, in its wild-type, un-attenuated state, can infect and cause disease and/or illness in an animal. "Disease and/or illness in an animal" includes adverse physical manifestations in an animal as well as clinical signs of disease or infection indicated solely by histological, microscopic and/or molecular diagnostics. Animal-pathogenic *Mycoplasma* bacteria include human- and non-human-pathogenic *Mycoplasma* bacteria. Human-pathogenic *Mycoplasma* bacteria include, but are not limited to, e.g., bacteria of the *Mycoplasma* species *M. genitalium, M. fermentans, M. salivarium, M. hominis, M. pneumonia, M. incognitus, M. penetrans, M. pirum, M. faucium, M. lipophilum*, and *M. buccale*. Non-human-pathogenic *Mycoplasma* bacteria include, e.g., avian-, porcine-, ovine-, bovine-, caprine- or canine-pathogenic *Mycoplasma* bacteria. Avian-pathogenic *Mycoplasma* bacteria include, but are not limited to, e.g., bacteria of the *Mycoplasma* species *M. cloacale, M. gallinarum, M. gallisepticum, M. gallopavonis, M. glycophilum, M. iners, M. iowae, M. lipofaciens, M. meleagridis*, and *M. synoviae*. Porcine-pathogenic *Mycoplasma* bacteria include, but are not limited to, e.g., bacteria of the *Mycoplasma* species *M. flocculare, M. hyopneumoniae, M. hyorhinis*, and *M. hyosynoviae*. Ovine-, bovine-, caprine- or canine-pathogenic *Mycoplasma* bacteria include, but are not limited to, e.g., bacteria of the *Mycoplasma* species *M. capricolumn* subsp. *capricolum, M. capricolumn* subsp. *capripneumoniae, M. mycoides* subsp. *mycoides* LC, *M. mycoides* subsp. *capri, M. bovis, M. bovoculi, M. canis, M. californicum*, and *M. dispar*.

In the method of the second aspect an initial population of *Mycoplasma* bacteria are subjected to attenuating conditions.

According to this aspect of the invention, the "initial population of *Mycoplasma* bacteria" can be any quantity of *Mycoplasma* bacteria. The bacteria, in certain embodiments are wild-type bacteria. Alternatively, the bacteria may contain one or more mutations. In one embodiment bacteria in the initial population are clonally identical or substantially clonally identical; that is, the bacteria preferably are all derived from a single parental *Mycoplasma* bacterial cell and/or have identical or substantially identical genotypic and/or phenotypic characteristics.

As used herein, the term "attenuating conditions" means any condition or combination of conditions which has/have the potential for introducing one or more genetic changes (e.g., nucleotide mutations) into the genome of a *Mycoplasma* bacterium. Exemplary, non-limiting, attenuating conditions include, e.g., passaging bacteria in culture, transforming bacteria with a genome-insertable genetic element such as a transposon (e.g., a transposon that randomly inserts into the

*Mycoplasma* genome), exposing bacteria to one or more mutagens (e.g., chemical mutagens or ultraviolet light), site directed mutagenesis or deletions etc. When bacterial cells are attenuated by passaging in vitro, the cells may be passaged any number of times, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, or more times in vitro.

The initial population of *Mycoplasma* cells, after being subjected to attenuating conditions, are referred to herein as a putatively attenuated bacterial population. Individual clones of the putatively attenuated bacterial population can be obtained by standard microbiological techniques including, e.g., serially diluting the cells and plating out individual cells on appropriate media. Once obtained, the individual clones of the putatively attenuated bacterial population are assayed for the presence of a mutation in at least one gene encoding a protein listed in Table 1 or in a nucleic acid molecule listed in any one of Tables 2 to 5. Methods for determining whether an attenuated *Mycoplasma* bacterium comprises a mutation are described elsewhere herein. Exemplary methods include, e.g., RT-PCR-based methods, Western blot, etc.

Individual clones identified as comprising at least one of the required mutations can be tested for virulence by administration of the clones to an animal that is susceptible to infection by the wild-type (unattenuated) version of the bacterium. As used herein, "an animal that is susceptible to infection by a wild-type *Mycoplasma* bacterium" is an animal that shows at least one clinical symptom after being challenged with a wild-type *Mycoplasma* bacterium. Such symptoms are known to persons of ordinary skill in the art. For example, in the case of a putatively attenuated *M. hyo* strain that exhibits a mutation in each of the proteins listed in Table 1 and each of the mutations listed in Tables 2 to 5, the strain can be administered to pigs (which are normally susceptible to infection by wild-type *M. hyo*). Clinical symptoms of *M. hyo* infection of pigs include, e.g., acute respiratory symptoms, and reduced weight gain. Thus, if the putatively attenuated *M. hyo* strain, when administered to a pig, results in fewer and/or less severe symptoms as compared to a pig that has been infected with a wild-type *M. hyo* strain, then the putatively attenuated *M. hyo* strain is deemed to have "reduced virulence." Any degree of reduction in symptoms will identify the putatively attenuated strain as having reduced virulence. In certain embodiments, the putatively attenuated strain will be avirulent.

The attenuated *Mycoplasma* bacteria of the third aspect can be used in a live vaccine.

The term "in vitro serial passaging" refers to the practice of repeated passage of bacteria in media. It involves inoculating a broth medium with a live bacterial culture which is then given some time to incubate at the appropriate temperature. A portion of the incubated culture is then used to inoculate a fresh sterile culture which in turn is given some time to incubate. The cycle continues to achieve the desired number of passages. Each round of growth and re-inoculation is referred to as a single passage.

The immunogenic composition of the fourth aspect comprises the attenuated *Mycoplasma* bacteria of the third aspect. This immunogenic composition may be used with a suitable carrier in the vaccine of the fifth aspect.

A vaccine is a biological preparation that establishes or improves immunity to a particular disease. Vaccines can be prophylactic (e.g. to prevent or ameliorate the effects of a future infection by the pathogen), or therapeutic (e.g. to treat the infection). The vaccine of the fifth aspect is prophylactic for a disease caused by a *Mycoplasma* bacteria.

The appropriate carrier will be evident to those skilled in the art and will depend in large part upon the route of administration. The vaccine may further comprise one or more additional ingredients including, but not limited to, suspending, stabilizing, or dispersing agents. Still additional components that may be present in the vaccine are adjuvants, preservatives, chemical stabilizers, or other antigenic proteins. Typically, stabilizers, adjuvants, and preservatives are optimized to determine the best formulation for efficacy in the target animal. Suitable exemplary preservatives include chlorobutanol potassium sorbate, sorbic acid, sulfur dioxide, propyl gallate, the parabens, ethyl vanillin, glycerin, phenol, and parachlorophenol. Suitable stabilizing ingredients which may be used include, for example, casamino acids, sucrose, gelatin, phenol red, N-Z amine, monopotassium diphosphate, lactose, lactalbumin hydrolysate, and dried milk. A conventional adjuvant is used to attract leukocytes or enhance an immune response. Such adjuvants include, among others, MPL™ (3-O-deacylated monophosphoryl lipid A; RIBI ImmunoChem Research, Inc., Hamilton, Mont.), mineral oil and water, aluminum hydroxide, Amphigen, Avridine, L121/squalene, D-lactide-polylactide/glycoside, pluronic plyois, muramyl dipeptide, killed Bordetella, saponins, such as Quil A or Stimulon™ QS-21 (Aquila Biopharmaceuticals, Inc., Framingham, Mass.) and cholera toxin (either in a wild-type or mutant form, e.g., wherein the glutamic acid at amino acid position 29 is replaced by another amino acid, preferably a histidine, in accordance with International Patent Application No. PCT/US99/22520).

In one embodiment, the vaccine, if injected has little or no adverse or undesired reaction at the site of the injection, e.g., skin irritation, swelling, rash, necrosis, skin sensitization.

The sixth aspect relates to protecting against disease caused by *Mycoplasma*. The vaccine of the fifth aspect is prophylactic for a disease caused by *Mycoplasma*.

"Prophylaxis" or "prophylactic" or "preventative" therapy or "protecting against" as referred to herein includes keeping the infection from occurring or to hinder or defend from or protect from the occurrence or severity of a disease caused by *Mycoplasma*, including preventing, protecting or lessening the severity of a symptom or feature of the disease in a subject that may be predisposed to the disease, but has not yet been diagnosed as having it. It also includes reducing the period of infection or incidence of symptoms and reducing the size of any lesions.

"Prophylaxis" as used herein covers total prevention of the disease or a reduction in the extent or symptoms of the disease. It also refers to the reduction or inhibition of transmission of *Mycoplasma* or preventing the bacteria establishing in the host or protection against secondary infection with other *Mycoplasma* strains or other infectious agents.

The vaccine of the fifth aspect may be prepared for administration to animals in the form of for example, liquids, powders, aerosols, tablets, capsules, enteric coated tablets or capsules, or suppositories. Routes of administration include, without limitation, parenteral administration, intraperitoneal administration, intravenous administration, intramuscular administration, subcutaneous administration, intradermal administration, oral administration, topical administration, intranasal administration, intra-pulmonary administration, rectal administration, vaginal administration, and the like.

In an embodiment in relation to *Mycoplasma* bacteria which infect the respiratory tract, the vaccine is formulated for administration to the respiratory tract, for example by intranasal administration, aerosol administration or administration by inhalation by the mouth or nose. This route of administration is preferred because the nature of protective immunity for *M. hyopneumoniae* may be local (pulmonary) immunity and cell-mediated immunity in preventing the disease rather than from circulating antibodies. Presentation of the vaccine to the respiratory tract may stimulate a local immune response. Therefore localised administration of the vaccine may be more effective. Furthermore by administering the vaccine in an enclosed barn or space (coarse spray mass administration) and allowing the pigs to inhale it, reduces the labour involved in vaccinating large numbers of animals. Aerosol vaccination (or spray vaccination) is currently used on a commercial basis to effectively vaccinate poultry against certain diseases and is also suitable for vaccinating pigs.

Intranasal administration covers any administration via the nasal passages or snout. The vaccine may be applied to the nasal cavity as a solution, suspension or dry powder. Solutions and suspensions may be administered intranasally using, for example, a pipette, a dropper or a spray, optionally an aerosol spray. Dry powders may be administered intranasally by inhalation.

Aerosol administration refers to administration of the vaccine in as a suspension of fine solid particles or liquid droplets in a gas.

Inhalation (also known as inspiration) is the movement of air from the external environment, through the air ways, and into the alveoli in the lungs.

An effective dose of vaccine to be employed therapeutically will depend, for example, upon the therapeutic objectives, the route of administration, and the condition of the animal.

Dosage levels for the vaccine will usually be of the order of about $10^3$ to $10^8$ colour changing units (CCU) per mL per dose, and preferably about $10^4$ to $10^7$ CCU per mL per dose.

It will be understood, however, that the specific dose level for any particular porcine animal will depend upon a variety of factors including the activity of the specific compound employed, the age, body weight, general health, sex, diet, time of administration and route of administration.

Selection and upward or downward adjustment of the effective dose is within the skill of the art.

Information about mutations in *Mycoplasma* bacteria that render a strain attenuated allow determination of whether an animal is infected with an attenuated or virulent *Mycoplasma* strain.

Wild type field strains infect animals and if they are virulent strains then they can cause disease in their own right or they can pave the way for secondary bacterial and/or viral infections.

Following infection, both the vaccine strain and any wild type *Mycoplasma* strain (through infection via natural exposure) can be recovered from the animal. Detection can be made by PCR. The organism can be extracted directly from infected tissues (e.g. from lung or trachea) and undergo detection by PCR. The organism recovered from the animal may be cultured in vitro first to allow the organism to grow so that more copies of the organism are present to increase effectiveness of detection methods (e.g. by PCR or via biochemical or serological methods for identification).

With respect to analysing outbreaks of infection, the method of the ninth aspect could determine whether or not the outbreak was due to a vaccine strain. That is, if an animal has been vaccinated with a *Mycoplasma* vaccine and soon develops disease, the subject can be tested to determine if it is vaccine or whether it is a wild type virulent field strain that is responsible for the infection. This is particularly important in a farm setting.

The ninth and tenth aspects provide kits comprising primers or probes for detecting mutations related to attenuation.

In one embodiment the primers are MHP-2F (SEQ ID NO:1) and MHP-2R (SEQ ID NO:2).

In another embodiment the primers are MHP-9/10-2F (SEQ ID NO:3) and MHP-9/10-2R (SEQ ID NO:4).

In one embodiment the kit comprises oligonucleotide probes that hybridise with the mutated gene or nucleic acid molecule. The probes may be labeled with a radioactive or non-radioactive labeling agent, the latter comprises conventional biotin, Dig (digoxigenin), FRET (fluorescence resonance energy transfer) or fluorescent dye (Cy5 or Cy3). Further, the oligonucleotides can be used as primers for PCR amplification. In this case, the kit may contain DNA polymerase, 4 dNTPs and PCR buffer for PCR reaction. In addition, the oligonucleotides can be attached to a microarray as probes. In this case, the kit may contain hybridization reaction buffer, PCR kit containing primers for amplifying a target gene, washing solution for the unhybridized DNA, dyes, washing solution for unbound dyes and manual sheet for the microarray.

In one embodiment, the probes may be a combination of more than one probe capable of simultaneously detecting more than one mutation from a single sample. Practically, the probes are optimized to simultaneously hybridize with multiple target mutation DNAs of *Mycoplasma* under the same hybridization and washing conditions.

In one embodiment the kit provides a microarray comprising a set of probes for detecting one or more mutations, which can simultaneously detect many mutations from a single sample with a single experiment.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It must also be noted that, as used in the subject specification, the singular forms "a", "an" and "the" include plural aspects unless the context clearly dictates otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

All references, including any patents or patent applications, cited in this specification are hereby incorporated by reference. It will be clearly understood that, although a number of prior art publications are referred to herein, this reference does not constitute an admission that any of these documents forms part of the common general knowledge in the art.

BRIEF DESCRIPTION OF FIGURES

FIG. 1A-C show the exact nature and location of mutations in the *M. hyo* ts-19 vaccine strain (master and P12) compared to the *M. hyo* J strain deposited as NC_007295.1 (SEQ ID NO:5) and the *M. hyo* LKR strain.

FIGS. 4A and B show high resolution melting (HRM) profile of genome target MHP9/10 in the normalized graph mode for Vaxsafe® MHP vaccine strain, parent strain and a mixture of these two strains. (B) Difference graph where the vaccine strain has been normalized such that any deviations from the vaccine strain can be observed.

Figure 2:
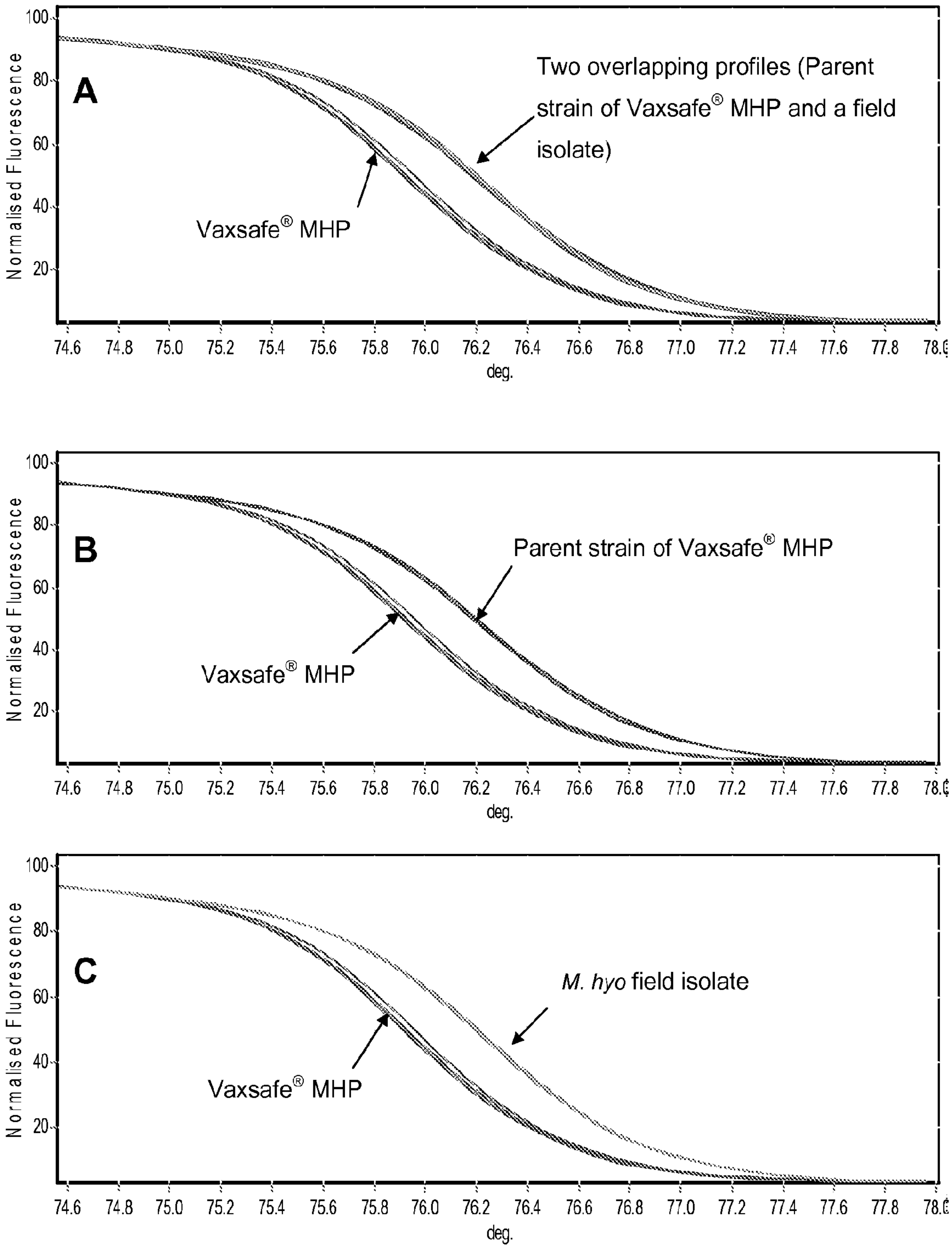
FIG. 2A-D show the high resolution melting (HRM) profile of genome target MHP2 in the normalized graph mode. (A) HRM of Vaxsafe® MHP strain, the parent strain of Vaxsafe®MHP and a field isolated strain of *M. hyo* (B) HRM of Vaxsafe® MHP strain and the parent strain of Vaxsafe® MHP (C) HRM of Vaxsafe® MHP strain and a field isolate strain (D) Difference graph where the wild-type strains have been normalized such that any deviations from the wild-type can be observed.
Figure 2:
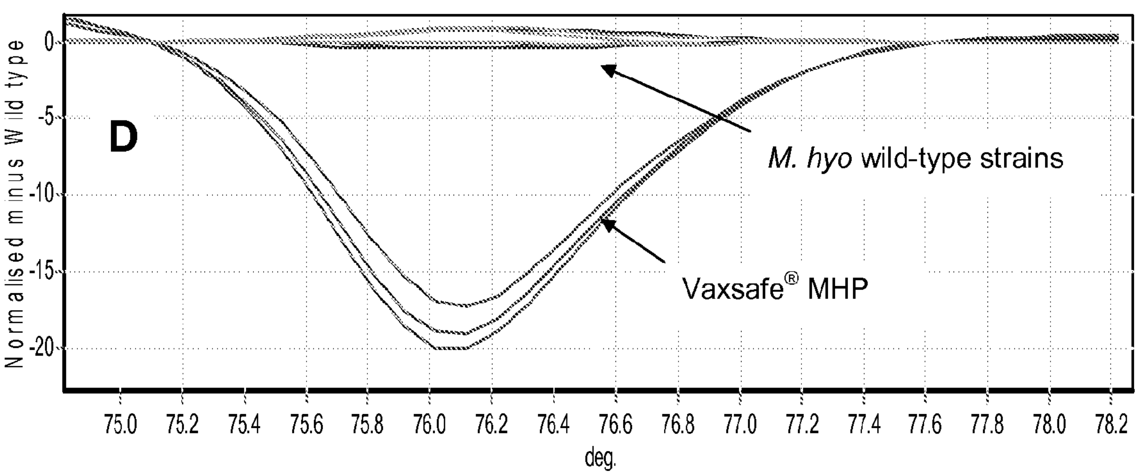

The invention is now further described in detail by reference to the following example. The example is provided for purposes of illustration only, and is not intended to be limiting unless otherwise specified. Thus, the invention encompasses any and all variations which become evident as a result of the teaching provided herein.

Example 1

Preparation of Vaccine Strain

Australian *Mycoplasma hyopneumoniae* isolate LKR is an abattoir specimen of pig lung exhibiting typical enzootic pneumonia disease (Lloyd and Etheridge (1981), J. Comp. Path. 91:77-83). The isolate was cultured and stored at the *Mycoplasma* reference culture collection at the University of Adelaide, South Australia. A culture of this isolate was subsequently obtained by the *Mycoplasma* group at the University of Melbourne, Victoria.

The culture was in vitro passaged three times before being subjected to mutagenesis using N-Methyl-N'-nitro-N-nitrosoguanidine (NTG) at 200 mg/mL using a method described previously (Nonamura and Imada (1982) Avian Diseases 26:763-775). Briefly, a culture of *M. hyopneumoniae* strain LKR was growth to late log phase and pelleted by centrifugation. The cells were washed in phosphate buffered saline (PBS) and exposed to NTG. The cells were pelleted and resuspended in modified Friis media (Friis, N. F. 1975) and incubated at 33° C. for 4 h. The culture was then passed through a 0.45 μm filter, appropriate dilutions made and aliquots placed onto agar plates and incubated at 33° C. Colonies that had grown were cloned into 3 mL of broth and incubated at 33° C. Ampoules of the clones were stored at −70° C. and the temperature sensitivity of each clone determined.

The temperature sensitivity of ts-19 was determined by performing a duplicate titration and incubation at 33° C. and 39.5° C. The titre is typically $>1\times10^8$ CCU/mL at 33° C. and $<1\times10^2$ CCU/mL at 39.5° C.

The ts-19 strain was deposited under the Budapest Treaty as NM 04/41259. It is used in Vaxsafe® MHP, a live attenuated temperature sensitive vaccine for protection against *M. hyopneumoniae* infection in pigs.

Example 2

Sequencing and Analysis

Whole genome sequencing for three *M. hyopneumoniae* strains (vaccine strains ts-19 Master, ts-19 P12 and the parental strain LKR) was performed. Sequencing was conducted by utilizing 454 sequencing technology (Roche). A minimum of 15× coverage per read was performed for each of the three genomes sequenced. For each separate genome, a consensus sequence was deduced from each set of reads. Overlapping reads for each genome were aligned into several large contigs. The contigs derived from the vaccine strain were determined through sequence alignment to have a high homology to the *M. hyopneumoniae* J strain sequence (NC_007295.1 (SEQ ID NO:5)).

The large contigs from each strain were then aligned against the J strain sequence and the gaps within the ts-19 or LRK sequences were subsequently identified. Several PCR primers spanning the gaps were designed and synthesised. The primer sequences were based on a combination of sequence generated from the vaccine or LKR strain or from the sequence of the J strain available on the nucleotide database (GENBANK, NC_007295.1 (SEQ ID NO:5)). The primers were used to amplify by PCR the target regions. The PCR amplicons were then sequenced. The sequences generated from overlapping reads spanning the gap regions were then aligned into a contig until the gaps were bridged and the whole genome sequence was subsequently completed.

Once the whole genome sequences of ts-19 (Master and P12) as well as the parental strain LKR was completed, the three sequences were then aligned against the full genome of J strain in a multiple sequence alignment.

From the multiple sequence alignment, nucleotide bases that were substituted, deleted or inserted from both the ts-19 Master and the P12 genomes when compared with both the sequences of the LKR and the J strain were identified as mutations. These mutations were categorized as changes within known genes, hypothetical genes, intergenic or non-coding regions. The proteins encoded by the mutated genes are listed in Table 1. Further mutations are listed in Tables 2 to 5. The exact nature and location of the mutations is show in FIG. 1.

Example 3

Selecting for Novel Attenuated *Mycoplasma*

Selection of a novel *Mycoplasma hyopneumoniae* or other *Mycoplasma* sp vaccine candidate(s) may be made by screening clones for one or more genes which have been mutated in ts-19.

Following mutagenesis and ts selection, a ts *Mycoplasma* clone would be grown in culture and the organism subjected to mRNA extraction using standard methods. The mRNA will be converted to cDNA using reverse transcriptase. The parent strain will also be grown in culture and the organism subjected to mRNA extraction. The mRNA will be converted to cDNA.

The cDNA from each of the ts clone and the parent strain will be used in separate PCR reactions targeting one or more of the mutated genes identified in ts-19. The resulting PCR amplicon(s) will be printed onto microarray slides. Two slides will be prepared encompassing the array of ts clone PCR products and two other slides will be prepared to encompass the array of parent PCR products.

The whole genome cDNA from the ts clone will then be coupled to a Cy Dye Ester (e.g. Cy3) and the whole genome cDNA from the parent will be coupled to another Cy Dye Ester (e.g. Cy4).

The Cy3 labelled cDNA will be hybridized to each of the microarray slides (one ts clone and one parent). Similarly the Cy4 labelled cDNA will be hybridized to each of the microarray slides (one ts clone and one parent).

Differential expression will analysed based on hybridization signal strength and colour which will be reflective of gene expression levels.

Example 4

Distinguishing Between Ts-19 and Other *M. hyo* in the Field

A field sample (e.g. nasal swab or lung tissue retrieved from the infected pig) will be subjected to PCR amplification using a specific set of primer(s). Each primer set will be designed to flank a different site of mutation identified to be unique to ts-19 vaccine strain. The PCR amplicon can be analysed by mutation detection techniques such as:

Fluorescent Capillary Electrophoresis (CE):

For deletion and insertion mutations, fluorescent CE would be a suitable mutation detection technique to employ. In this case the PCR primers would each be labelled with a different fluorophore and used in a PCR reaction. The field sample (test) as well as a ts-19 sample (positive control) will undergo PCR amplification. The PCR products generated from the field test sample and the positive control (ts-19) would be subjected to capillary electrophoresis whereby the separation of PCR product is based on size. CE can identify changes in amplicon size resulting from a single (or multiple) nucleotide base deletion or insertion. Therefore a PCR amplicon from the vaccine strain would have a known peak position which will be different to the PCR amplicon generated from the field sample. If both the ts-19 vaccine and a field strain are present in the sample, then two distinct peaks will be observed.

Single Strand Conformation Polymorphism (SSCP):

Single-strand conformation polymorphism (SSCP) analysis is a sensitive technique for mutation detection. The principle of SSCP analysis is based on the fact that single-stranded DNA has a defined conformation. Altered conformation due to a single base change in the sequence can cause single-stranded DNA to migrate differently under non-denaturing electrophoresis conditions. Therefore, PCR from the ts-19 vaccine strain (positive control) and that of the field test sample(s) will display different banding patterns.

SSCP can be applied for base changes, deletions and insertions. One or more mutation regions can be PCR amplified using radioactively labelled primer (e.g. labelled with $P^{33}$). A ts-19 positive control amplicon sample is assayed in an identical manner to the field test sample. The double stranded DNA amplicons undergo denaturing (i.e. exposure to heat and alkaline) will result in the formation of single stranded DNA molecules which are immediately subjected to electrophoresis separation under non-denaturing conditions. Following electrophoresis, the gel will be dried onto filter paper (e.g. Whatmann) and then exposed to autoradiographic film. Following development of the autoradiograph the banding patterns from the field sample will be compared with that of the ts-19 positive control sample. An identical banding pattern to the ts-19 pattern will indicate that the sample is ts-19 vaccine strain. A different banding pattern will indicate that the sample is not ts-19.

The SSCP method may also be applied in a non-radioactive format.

High Resolution Melt (HRM) Curve Analysis:

HRM curve analysis will be applicable for mutations involving base substitutions, deletions and insertions. In this case the field test sample as well as a ts-19 positive control sample will be subjected to real time (RT) PCR amplification of a unique (mutation containing) region using a cycle sequencer. The PCR machine used will be one capable of performing HRM curve analysis. At the completion of the PCR amplification cycle the PCR amplicon will be subjected to a HRM curve analysis conducted by the PCR machine. The ts-19 amplicon will display a distinguished melt curve display compared to the field strain amplicon.

Example 5

HRM Analysis for Vaxsafe® MHP

Based on the mutation data from Example 2 two examples of high resolution melt curve (HRM) assays have been developed that are capable of distinguishing between Vaxsafe® MHP vaccine strain and other *M. hyo* strains including the vaccine parental strain. However, any of the mutational changes present within the vaccine strain can be used as targets for HRM analysis.

Two regions within the vaccine genome were chosen as an example for HRM analysis. These regions are designated MHP2 and MHP9/10. MHP2 is an example of HRM targeting a single mutation (FIGS. 1B and C mutation number 2). MHP9/10 is an example of HRM targeting two mutations (FIGS. 1B and C mutation numbers 9 and 10). The Qiagen "Rotor Gene Q" unit with 2 or 5 Plex and HRM capability was used in this work in conjunction with the Type-It® HRM™ kit. In brief, HRM is a post-PCR technique which can be used for mutation scanning and genotyping. The method does not require post-PCR handling and hence minimises the risk of cross-contamination. Furthermore, there is no separation step involved and this reduces analysis time.

HMR analysis is conducted on DNA samples such as clinical samples (eg. swabs or tissue preparations) cultured for *M. hyopneumoniae* in selective broth media to minimise growth of contaminating organisms. The DNA is then extracted from cultured *M. hyo* samples. The purified DNA is normalized for all test samples.

Example 5a

Target MHP2

The primer sets (MHP-2F and MHP-2R) were chosen to amplify a 151 bp region of the *M. hyopneumoniae* genome.

| Primer Name | Sequence (5'→3') | Amplicon Size (bp) |
|---|---|---|
| MHP-2F | GAC AAG GAA CCA AGC GTT TC (SEQ ID NO: 1) | 151 |
| MHP-2R | CAG GCT CTT GCA TTT TAC AGT C (SEQ ID NO: 2) | |

PCR Reaction

The HRM reactions are conducted in triplicate. Each reaction contains the following:

| | |
|---|---|
| HRM PCR Super Mix (2x) | 12.5 μl |
| Nuclease free water | 9.75 μl |
| Forward Primer (10 pmol/μL) | 0.9 μl |
| Reverse Primer (10 pmol/μL) | 0.9 μl |
| DNA template (70 pg/μL) | 1 μl |

Dispense the required reagents (see above) into a 0.1 mL PCR tubes and subject to thermal cycling.

Thermal Cycling Conditions:

| Cycle | Cycle Point |
| --- | --- |
| Hold @ 95° C., 5 min 0 secs | |
| Cycling (40 repeats) | Step 1 @ 95° C., hold 10 secs<br>Step 2 @ 55° C., hold 30 secs<br>Step 3 @ 72° C., hold 10 secs, acquiring to Cycling A([Green][1][1]) |
| Melt (68-87° C.), hold secs on the 1st step, hold 2 secs on next steps, Melt A([HRM][7][1]) | HRM Analysis, data acquisition every 0.1° C. |

Results

HRM analysis was performed on DNA extracted from pure cultures of either the vaccine or other *M. hyo* strains. Individual reactions were performed on either DNA from each strain or on mixture of DNA from different strains.

The HRM profiles of target MHP2 for Vaxsafe© MHP vaccine strain and two wild-type *M. hyo* (vaccine parent strain and a field isolated strain) are shown in FIGS. 2 (A, B and C). The HRM exhibited a melting pattern that started its separation at approximately 75.2° C. and ended at approximately 77.4° C. The vaccine strain showed a lower temperature melting profile, resulting in its separation from both wild type strains (the parent strain of Vaxsafe® MHP and the field isolated strain). The wild-type strains maintained a higher level of fluorescence for a longer period of time than the vaccine strain resulting in a melting profile that is shifted to the right. This shift can be used to distinguish between the vaccine strain and other *M. hyo* wild-type strains.

The HRM profiles of the two *M. hyo* wild-type strains were identical as shown by their overlapping profiles (FIG. 2A). The overlapped profiles are shown separately in FIGS. 2B and C. FIG. 2D displays the same data using a "difference graph" which shows a clear separation between the vaccine strain and the wild type strains. The difference graph is created by defining the vaccine strain as the reference. The fluorescence levels of the wild-type strains are then normalized to ~zero and any deviations from the wild-type standard are recorded in the difference graph.

Example 5b

Target MHP9/10

The primer sets (MHP-9/10-2F and MHP-9/10-2R) were chosen to amplify a 160 bp region of the *M. hyopneumoniae* genome.

| Primer Name | Sequence (5'→3') | Amplicon Size (bp) |
| --- | --- | --- |
| MHP-9/10-2F | TGT CAA GAA CAT AAG ATG GAG TTC A (SEQ ID NO: 3) | 160 |
| MHP-9/10-2R | ATT GTC GAA TCC CCT AAT AAA AT (SEQ ID NO: 4) | |

PCR Reaction

The HRM reactions are conducted in triplicate. Each reaction contains the following:

| | |
| --- | --- |
| HRM PCR Super Mix (2x) | 12.5 µl |
| Nuclease free water | 9.75 µl |
| Forward Primer (10 pmol/µL) | 0.9 µl |

-continued

| | |
| --- | --- |
| Reverse Primer (10 pmol/µL) | 0.9 µl |
| DNA template (70 pg/µL) | 1 µl |

Dispense the required reagents (see above) into a 0.1 mL PCR tubes and subject to thermal cycling.

Thermal Cycling Conditions:

| Cycle | Cycle Point |
| --- | --- |
| Hold @ 95° C., 5 min 0 secs | |
| Cycling (40 repeats) | Step 1 @ 95° C., hold 10 secs<br>Step 2 @ 55° C., hold 30 secs<br>Step 3 @ 72° C., hold 10 secs, acquiring to Cycling A([Green][1][1]) |
| Melt (68-87° C.), hold secs on the 1st step, hold 2 secs on next steps, Melt A([HRM][7][1]) | HRM Analysis, data acquisition every 0.1° C. |

Figure 3:
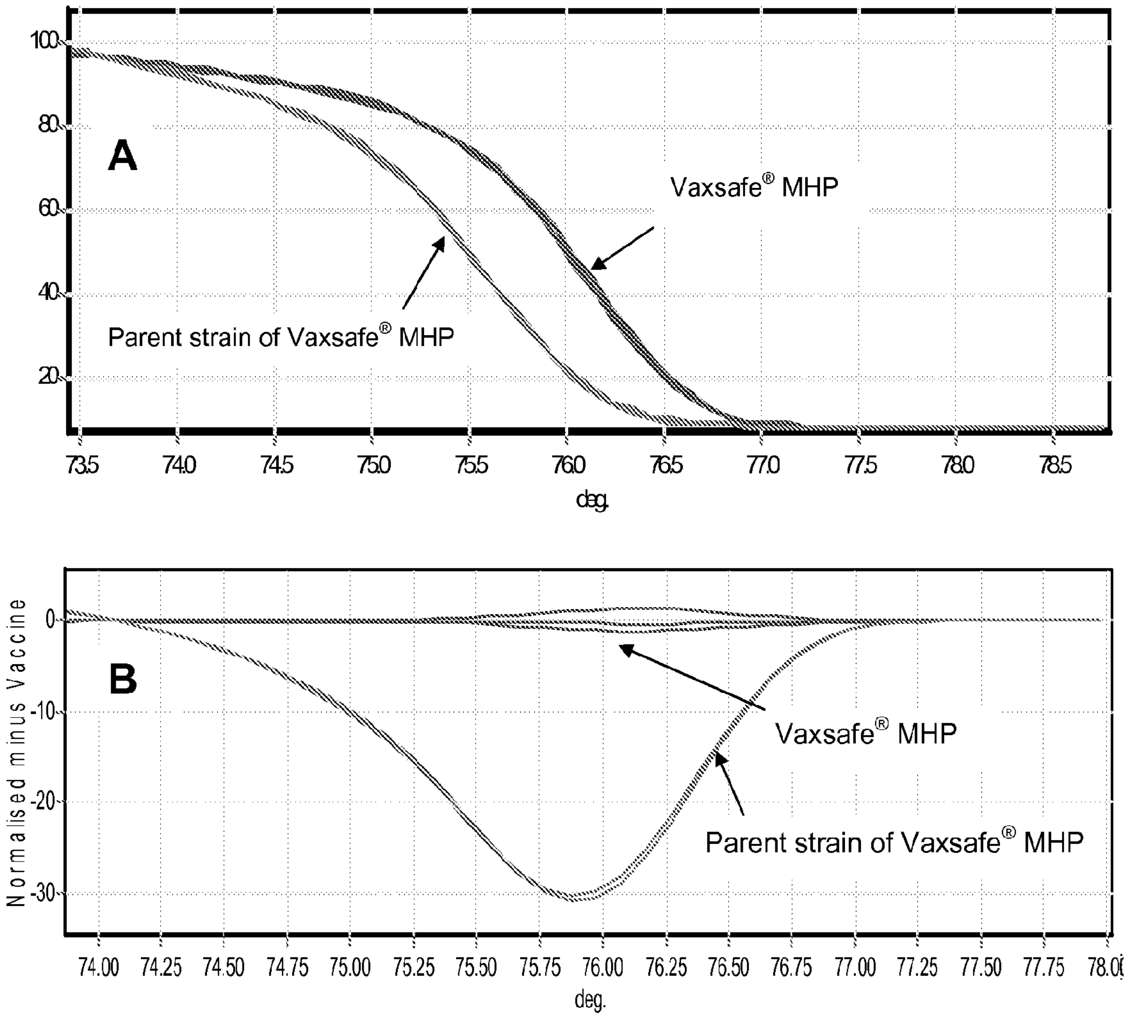
FIGS. 3A and B show the high resolution melting (HRM) profile of genome target MHP9/10 in the normalized graph mode for Vaxsafe® MHP vaccine strain and parent strain. (B) Difference graph where the vaccine strain has been normalized such that any deviation from the vaccine can be observed.

The HRM profiles of target MHP9/10 for Vaxsafe MHP vaccine strain and the parent strain are shown in FIG. 3A. The HRM exhibited a melting pattern that commenced separation at approximately 73.7° C. and ended at approximately 77.0° C. The vaccine strain showed a higher temperature melting profile, resulting in its differentiation from the parent strain. The vaccine strain maintained a higher level of fluorescence for a longer period of time than the parent strain resulting in a melting profile that is shifted to the right. This shift can be used to distinguish between the vaccine strain and the parent strain. FIG. 3B displays the same data using a "difference graph" which shows a clear separation between the vaccine strain and the parent strain.

DNA from both Vaxsafe® MHP vaccine strain and a parent *M. hyo* strain LKR were mixed on a ratio of 1:1 and subjected to HRM analysis for target MHP9/10. In the same analysis individual DNA from each strain was also subjected to HRM analysis. The profiles (FIG. 4A) exhibited the same melting pattern as described above for target MHP9/10 allowing the distinction between the vaccine strain and the parent strain. The HRM profiles of the mixed *M. hyo* DNA (vaccine and parent strains) shown in FIG. 4 (A) exhibited a melting pattern which is different from both the DNA of the individual vaccine and parent strains. In the difference graph (FIG. 4B) the vaccine strain has been normalized such that any deviations from the vaccine can be observed. In the difference graphs the vaccine can be distinguished from the wild type strain but the mixture sample exhibited a totally different melting profile to both the wild type and vaccine strain (FIG. 4B).

CONCLUSIONS

Two examples were chosen to demonstrate that HRM curve analysis can be used as a tool to differentiate between Vaxsafe® MHP vaccine strain and other *M. hyo* wild-type strains including the vaccine parent strain. Example 5a demonstrated differentiation based on a single nucleotide base. Example 5b demonstrated differentiation based on two nucleotide base changes. HRM analysis can subsequently be used to target any of the numerous mutational changes present in the vaccine strain as a means for differentiation of infected from vaccinated animals (DIVA). A single HRM analysis can target either a single or multiple mutations. For each mutation(s) the forward primer can be designed anywhere within a 500 bp region upstream of the mutation site(s). The reverse primer can be designed anywhere within a 500 bp region downstream of the mutation site(s). Preferably the resulting amplicon should be between 50-200 bp in size.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09260691B2). An electronic copy of the "Sequence Listing" will also be available from the USPTO upon request and payment of the fee set forth in 37 CFR 1.19(b)(3).

The invention claimed is:

1. A method for identifying the presence of *Mycoplasma hyopneumoniae* bacterium strain ts-19 in a sample, the method comprising:

assaying the sample comprising *Mycoplasma hyopneumoniae* bacteria for the presence or absence of a nucleic acid molecule with a mutation selected from the group consisting of:

a GidA gene [tRNA uridine 5-carboxymethylaminomethyl modification enzyme] mutation, wherein an adenine at nucleotide 3075 of a *Mycoplasma hyopneumoniae* J strain sequence provided as SEQ ID NO: 5 is not present causing a frameshift mutation in a protein encoded by the nucleic acid molecule;

a mutation in a hypothetical protein, wherein an adenine at nucleotide 7324 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein a thymine at nucleotide 17143 of a *Mycoplasma hyopneumoniae* J strain sequence provided as SEQ ID NO:5 is not present;

an isoleucyl tRNA synthetase mutation, wherein a thymine at nucleotide 31773 of a *Mycoplasma hyopneumoniae* J strain sequence provided as SEQ ID NO: 5 is not present causing a frameshift mutation in a protein encoded by the nucleic acid molecule;

a GTPase ObgE mutation, wherein an adenine at nucleotide 48566 of a *Mycoplasma hyopneumoniae* J strain sequence provided as SEQ ID NO: 5 is not present causing a frameshift mutation in a protein encoded by the nucleic acid molecule;

a mutation in an intergenic sequence, wherein an adenine at nucleotide 48881 of a *Mycoplasma hyopneumoniae* J strain sequence provided as SEQ ID NO:5 is not present;

a DNA polymerase IV mutation, wherein an adenine at nucleotide 51166 of a *Mycoplasma hyopneumoniae* J strain sequence provided as SEQ ID NO: 5 is not present causing a frameshift mutation in a protein encoded by the nucleic acid molecule;

a mutation in an intergenic sequence, wherein a thymine at nucleotide 59567 of a *Mycoplasma hyopneumoniae* J strain sequence provided as SEQ ID NO:5 is not present;

a mutation in an intergenic sequence, wherein an adenine at nucleotide 66347 of a *Mycoplasma hyopneumoniae* J strain sequence provided as SEQ ID NO:5 is not present;

a mutation in a hypothetical protein, wherein an adenine at nucleotide 75037 of a *Mycoplasma hyopneumoniae* J strain sequence provided as SEQ ID NO: 5 is deleted causing a frameshift mutation in a protein encoded by the nucleic acid molecule;

an exonuclease ABC subunit C mutation, wherein a thymine at nucleotide 79461 of a *Mycoplasma hyopneumoniae* J strain sequence provided as SEQ ID NO: 5 is not present causing a frameshift mutation in a protein encoded by the nucleic acid molecule;

a mutation in a hypothetical protein, wherein a thymine at nucleotide 86810 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein an adenine at nucleotide 89715 of a *Mycoplasma hyopneumoniae* J strain sequence provided as SEQ ID NO:5 is not present;

a mutation in an intergenic sequence, wherein an adenine at nucleotide 94740 of a *Mycoplasma hyopneumoniae* J strain sequence provided as SEQ ID NO:5 is not present;

a mutation in an intergenic sequence, wherein a thymine at nucleotide 94742 of a *Mycoplasma hyopneumoniae* J strain sequence provided as SEQ ID NO:5 is not present;

a mutation in an intergenic sequence, wherein a thymine at nucleotide 104392 of a *Mycoplasma hyopneumoniae* J strain sequence provided as SEQ ID NO:5 is not present;

a mutation in an intergenic sequence, wherein an adenine at nucleotide 104393 of a *Mycoplasma hyopneumoniae* J strain sequence provided as SEQ ID NO:5 is not present;

a mutation in an intergenic sequence, wherein an adenine at nucleotide 117390 of a *Mycoplasma hyopneumoniae* J strain sequence provided as SEQ ID NO:5 is not present;

a mutation in a hypothetical protein, wherein an adenine at nucleotide 118681 of a *Mycoplasma hyopneumoniae* J strain sequence provided as SEQ ID NO: 5 is deleted causing a frameshift mutation in a protein encoded by the nucleic acid molecule;

a mutation in a hypothetical protein, wherein an adenine at nucleotide 118716 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein an adenine at nucleotide 120943 of a *Mycoplasma hyopneumoniae* J strain sequence provided as SEQ ID NO: 5 is not present;

a putative outer membrane protein P95 mutation, wherein an adenine at nucleotide 125147 of a *Mycoplasma hyopneumoniae* J strain sequence provided as SEQ ID NO: 5 is not present causing a frameshift mutation in a protein encoded by the nucleic acid molecule;

a triosephosphate isomerase mutation, wherein an adenine at nucleotide 131715 of a *Mycoplasma hyopneumoniae* J strain sequence provided as SEQ ID NO: 5 is not present causing a frameshift mutation in a protein encoded by the nucleic acid molecule;

a mutation in an intergenic sequence, wherein a thymine at nucleotide 133772 of a *Mycoplasma hyopneumoniae* J strain sequence provided as SEQ ID NO:5 is not present;

a mutation in an intergenic sequence, wherein an adenine at nucleotide 147361 of a *Mycoplasma hyopneumoniae* J strain sequence provided as SEQ ID NO:5 is not present;

a mutation in an intergenic sequence, wherein a thymine at nucleotide 153557 of a *Mycoplasma hyopneumoniae* J strain sequence provided as SEQ ID NO:5 is not present;

a mutation in a hypothetical protein, wherein an adenine at nucleotide 155557 of a *Mycoplasma hyopneumoniae* J strain sequence provided as SEQ ID NO: 5 is deleted causing a frameshift mutation in a protein encoded by the nucleic acid molecule;

a mutation in a hypothetical protein, wherein an adenine at nucleotide 157051 of a *Mycoplasma hyopneumoniae* J strain sequence provided as SEQ ID NO: 5 is deleted causing a frameshift mutation in a protein encoded by the nucleic acid molecule;

a uracil-DNA glycosylase mutation, wherein an adenine at nucleotide 163824 of a *Mycoplasma hyopneumoniae* J strain sequence provided as SEQ ID NO: 5 is not present causing a frameshift mutation in a protein encoded by the nucleic acid molecule;

a mutation in an intergenic sequence, wherein a thymine at nucleotide 170370 of a *Mycoplasma hyopneumoniae* J strain sequence provided as SEQ ID NO:5 is not present;

a putative chromate transport protein mutation, wherein a thymine at nucleotide 178555 of a *Mycoplasma hyopneumoniae* J strain sequence provided as SEQ ID NO: 5 is not present causing a frameshift mutation in a protein encoded by the nucleic acid molecule;

a mutation in a hypothetical protein, wherein a thymine at nucleotide 183981 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein an adenine at nucleotide 187424 of a *Mycoplasma hyopneumoniae* J strain sequence provided as SEQ ID NO:5 is not present;

a mutation in an intergenic sequence, wherein an adenine at nucleotide 187449 of a *Mycoplasma hyopneumoniae* J strain sequence provided as SEQ ID NO:5 is not present;

a putative ABC transporter ATP binding and permease protein mutation, wherein an adenine at nucleotide 190701 of a *Mycoplasma hyopneumoniae* J strain sequence provided as SEQ ID NO: 5 is not present causing a frameshift mutation in a protein encoded by the nucleic acid molecule;

a 50S ribosomal protein L3 mutation, wherein a thymine at nucleotide 212677 of a *Mycoplasma hyopneumoniae* J strain sequence provided as SEQ ID NO:5 is not present;

a mutation in a hypothetical protein, wherein an adenine at nucleotide 214047 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein an adenine at nucleotide 214362 of a *Mycoplasma hyopneumoniae* J strain sequence provided as SEQ ID NO:5 is not present;

a mutation in a hypothetical protein, wherein a thymine at nucleotide 226284 of a *Mycoplasma hyopneumoniae* J strain sequence provided as SEQ ID NO: 5 is deleted causing a frameshift mutation in a protein encoded by the nucleic acid molecule;

a mutation in a hypothetical protein, wherein an adenine at nucleotide 234616 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein a thymine at nucleotide 235499 of a *Mycoplasma hyopneumoniae* J strain sequence provided as SEQ ID NO:5 is not present;

a mutation in an intergenic sequence or a putative lipoprotein mutation, wherein an adenine at nucleotide 246806 of a *Mycoplasma hyopneumoniae* J strain sequence provided as SEQ ID NO: 5 is not present;

a putative lipoprotein (MHJ_0213) mutation, wherein an adenine at nucleotide 246808 of a *Mycoplasma hyopneumoniae* J strain sequence provided as SEQ ID NO: 5 is not present causing a frameshift mutation in a protein encoded by the nucleic acid molecule;

a ribonucleotide-disulphate reductase subunit alpha mutation, wherein a thymine at nucleotide 252401 of a *Mycoplasma hyopneumoniae* J strain sequence provided as SEQ ID NO: 5 is not present causing a frameshift mutation in a protein encoded by the nucleic acid molecule;

a mutation in a hypothetical protein, wherein a thymine at nucleotide 271614 of a *Mycoplasma hyopneumoniae* J strain sequence provided as SEQ ID NO: 5 is deleted causing a frameshift mutation in a protein encoded by the nucleic acid molecule;

a mutation in a hypothetical protein, wherein an adenine at nucleotide 293668 of a *Mycoplasma hyopneumoniae* J strain sequence provided as SEQ ID NO: 5 is deleted causing a frameshift mutation in a protein encoded by the nucleic acid molecule;

a thymidylate kinase mutation, wherein an adenine at nucleotide 300092 of a *Mycoplasma hyopneumoniae* J strain sequence provided as SEQ ID NO: 5 is not present causing a frameshift mutation in a protein encoded by the nucleic acid molecule;

a thymidylate kinase mutation, wherein an adenine at nucleotide 300098 of a *Mycoplasma hyopneumoniae* J strain sequence provided as SEQ ID NO: 5 is not present causing a frameshift mutation in a protein encoded by the nucleic acid molecule;

a DNA polymerase III subunit delta mutation, wherein an adenine at nucleotide 300772 of a *Mycoplasma hyopneumoniae* J strain sequence provided as SEQ ID NO: 5 is not present causing a frameshift mutation in a protein encoded by the nucleic acid molecule;

a DNA ligase mutation, wherein a thymine at nucleotide 305732 of a *Mycoplasma hyopneumoniae* J strain sequence provided as SEQ ID NO: 5 is not present causing a frameshift mutation in a protein encoded by the nucleic acid molecule;

a CDP-diacylglycerol-3-phosphate-3-phosphatidyl transferase mutation, wherein an adenine at nucleotide 328394 of a *Mycoplasma hyopneumoniae* J strain sequence provided as SEQ ID NO: 5 is not present causing a frameshift mutation in a protein encoded by the nucleic acid molecule;

a mutation in an intergenic sequence, wherein a thymine at nucleotide 410563 of a *Mycoplasma hyopneumoniae* J strain sequence provided as SEQ ID NO:5 is not present;

a mutation in a hypothetical protein, wherein a thymine at nucleotide 412710 of a *Mycoplasma hyopneumoniae* J strain sequence provided as SEQ ID NO: 5 is deleted causing a frameshift mutation in a protein encoded by the nucleic acid molecule;

a mutation in a hypothetical protein, wherein an adenine at nucleotide 413717 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein an adenine at nucleotide 426313 of a *Mycoplasma hyopneumoniae* J strain sequence provided as SEQ ID NO:5 is not present;

a mutation in an intergenic sequence, wherein an adenine at nucleotide 431650 of a *Mycoplasma hyopneumoniae* J strain sequence provided as SEQ ID NO:5 is not present;

a mutation in an intergenic sequence, wherein a thymine at nucleotide 431669 of a *Mycoplasma hyopneumoniae* J strain sequence provided as SEQ ID NO:5 is not present;

a putative ABC transport system permease protein p69-like mutation, wherein a thymine at nucleotide 437234 of a *Mycoplasma hyopneumoniae* J strain sequence provided as SEQ ID NO: 5 is not present causing a frameshift mutation in a protein encoded by the nucleic acid molecule;

a putative lipoprotein (MHJ_0362) mutation, wherein an adenine at nucleotide 442618 of a *Mycoplasma hyopneumoniae* J strain sequence provided as SEQ ID NO: 5 is not present causing a frameshift mutation in a protein encoded by the nucleic acid molecule;

a putative ABC transporter permease protein mutation, wherein an adenine at nucleotide 465533 of a *Mycoplasma hyopneumoniae* J strain sequence provided as SEQ ID NO: 5 is not present causing a frameshift mutation in a protein encoded by the nucleic acid molecule;

a mutation in an intergenic sequence, wherein an adenine at nucleotide 491786 of a *Mycoplasma hyopneumoniae* J strain sequence provided as SEQ ID NO:5 is not present;

a mutation in an intergenic sequence, wherein a thymine at nucleotide 502594 of a *Mycoplasma hyopneumoniae* J strain sequence provided as SEQ ID NO:5 is not present;

a mutation in a hypothetical protein, wherein a thymine at nucleotide 512112 of a *Mycoplasma hyopneumoniae* J strain sequence provided as SEQ ID NO: 5 is deleted causing a frameshift mutation in a protein encoded by the nucleic acid molecule;

a transketolase mutation, wherein an adenine at nucleotide 519298 of a *Mycoplasma hyopneumoniae* J strain sequence provided as SEQ ID NO: 5 is not present causing a frameshift mutation in a protein encoded by the nucleic acid molecule;

a mutation in a hypothetical protein, wherein a thymine at nucleotide 534108 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein an adenine at nucleotide 539244 of a *Mycoplasma hyopneumoniae* J strain sequence provided as SEQ ID NO:5 is not present;

a mutation in a hypothetical protein, wherein a thymine at nucleotide 558831 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein a thymine at nucleotide 564250 of a *Mycoplasma hyopneumoniae* J strain sequence provided as SEQ ID NO:5 is not present;

a mutation in a hypothetical protein, wherein an adenine at nucleotide 569870 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein a thymine at nucleotide 586142 of a *Mycoplasma hyopneumoniae* J strain sequence provided as SEQ ID NO:5 is not present;

a mutation in a hypothetical protein, wherein a thymine at nucleotide 591871 of a *Mycoplasma hyopneumoniae* J strain sequence provided as SEQ ID NO: 5 is deleted causing a frameshift mutation in a protein encoded by the nucleic acid molecule;

a mutation in a hypothetical protein, wherein a thymine at nucleotide 608132 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein an adenine at nucleotide 613911 of a *Mycoplasma hyopneumoniae* J strain sequence provided as SEQ ID NO:5 is not present;

a mutation in a hypothetical protein, wherein a thymine at nucleotide 615804 of a *Mycoplasma hyopneumoniae* J strain sequence provided as SEQ ID NO: 5 is deleted causing a frameshift mutation in a protein encoded by the nucleic acid molecule;

a putative P216 surface protein mutation, wherein a TTG codon is inserted at nucleotides 625870-625872 of a *Mycoplasma hyopneumoniae* J strain sequence provided as SEQ ID NO: 5 inserting a glutamine into a protein encoded by the nucleic acid molecule;

a putative p216 surface protein mutation, wherein a thymine at nucleotide 628031 of a *Mycoplasma hyopneumoniae* J strain sequence provided as SEQ ID NO: 5 is not present causing a frameshift mutation in a protein encoded by the nucleic acid molecule;

a mutation in an intergenic sequence, wherein an adenine at nucleotide 634595 of a *Mycoplasma hyopneumoniae* J strain sequence provided as SEQ ID NO:5 is not present;

DNA gyrase subunit A mutation, wherein an adenine at nucleotide 683823 of a *Mycoplasma hyopneumoniae* J strain sequence provided as SEQ ID NO: 5 is not present causing a frameshift mutation in a protein encoded by the nucleic acid molecule;

a mutation in a hypothetical protein, wherein an adenine at nucleotide 699407 of a *Mycoplasma hyopneumoniae* J strain sequence provided as SEQ ID NO: 5 is deleted causing a frameshift mutation in a protein encoded by the nucleic acid molecule;

a mutation in a hypothetical protein, wherein a thymine at nucleotide 699923 of a *Mycoplasma hyopneumoniae* J strain sequence provided as SEQ ID NO: 5 is deleted causing a frameshift mutation in a protein encoded by the nucleic acid molecule;

a mutation in a hypothetical protein, wherein a thymine at nucleotide 737657 of a *Mycoplasma hyopneumoniae* J strain sequence provided as SEQ ID NO: 5 is deleted causing a frameshift mutation in a protein encoded by the nucleic acid molecule;

a mutation in an intergenic sequence, wherein an adenine at nucleotide 748454 of a *Mycoplasma hyopneumoniae* J strain sequence provided as SEQ ID NO:5 is not present;

a ribonuclease H11 mutation, wherein an adenine at nucleotide 768571 of a *Mycoplasma hyopneumoniae* J strain sequence provided as SEQ ID NO: 5 is not present causing a frameshift mutation in a protein encoded by the nucleic acid molecule;

an inorganic pyrophosphatase mutation, wherein an adenine at nucleotide 785221 of a *Mycoplasma hyopneumoniae* J strain sequence provided as SEQ ID NO: 5 is not present causing a frameshift mutation in a protein encoded by the nucleic acid molecule;

a mutation in an intergenic sequence, wherein an adenine at nucleotide 810058 of a *Mycoplasma hyopneumoniae* J strain sequence provided as SEQ ID NO:5 is not present;

a mutation in an intergenic sequence, wherein an adenine at nucleotide 810061 of a *Mycoplasma hyopneumoniae* J strain sequence provided as SEQ ID NO:5 is not present;

a putative ABC transporter ATP binding Pr1 mutation, wherein a thymine at nucleotide 817687 of a *Mycoplasma hyopneumoniae* J strain sequence provided as SEQ ID NO: 5 is not present causing a frameshift mutation in a protein encoded by the nucleic acid molecule;

a putative adhesion like protein P146 mutation, wherein a thymine at nucleotide 875082 of a *Mycoplasma hyopneumoniae* J strain sequence provided as SEQ ID NO: 5 is not present causing a frameshift mutation in a protein encoded by the nucleic acid molecule;

a mutation in an intergenic sequence, wherein a thymine at nucleotide 883049 of a *Mycoplasma hyopneumoniae* J strain sequence provided as SEQ ID NO:5 is not present;

a putative MgpA-like protein mutation, wherein a guanine at nucleotide 6060 of a *Mycoplasma hyopneumoniae* J strain sequence provided as SEQ ID NO: 5 is substituted by an adenine;

a mutation in a hypothetical protein, wherein a guanine at nucleotide 10909 of a *Mycoplasma hyopneumoniae* J strain sequence provided as SEQ ID NO: 5 is substituted by an adenine causing an alanine to threonine substitution in a protein encoded by the nucleic acid molecule;

a mutation in an intergenic sequence between an amino acid permease and NADH oxidase, wherein an adenine at nucleotide 96181 of a *Mycoplasma hyopneumoniae* J strain sequence provided as SEQ ID NO: 5 is substituted by a guanine;

a mutation in a hypothetical protein, wherein an adenine at nucleotide 118293 of a *Mycoplasma hyopneumoniae* J strain sequence provided as SEQ ID NO: 5 is substituted by a guanine causing an aspartate to glycine substitution in a protein encoded by the nucleic acid molecule;

a putative outer membrane protein P95 mutation, wherein a guanine at nucleotide 123175 of a *Mycoplasma hyopneumoniae* J strain sequence provided as SEQ ID NO: 5 is substituted by a thymine causing a valine to phenylalanine substitution in a protein encoded by the nucleic acid molecule;

a uracil-DNA glycolase mutation, wherein a guanine at nucleotide 163911 of a *Mycoplasma hyopneumoniae* J strain sequence provided as SEQ ID NO: 5 is substituted by an adenine causing a serine to phenylalanine substitution in a protein encoded by the nucleic acid molecule;

a mutation in a hypothetical protein, wherein a guanine at nucleotide 246307 of a *Mycoplasma hyopneumoniae* J strain sequence provided as SEQ ID NO: 5 is substituted by a thymine causing a glycine to cysteine substitution in a protein encoded by the nucleic acid molecule;

a myo-inositol catabolism protein mutation, wherein a guanine at nucleotide 259905 of a *Mycoplasma hyopneumoniae* J strain sequence provided as SEQ ID NO: 5 is substituted by an adenine;

a DNA tropoisomerase I mutation, wherein an adenine at nucleotide 330948 of a *Mycoplasma hyopneumoniae* J strain sequence provided as SEQ ID NO: 5 is substituted by a guanine;

a DNA tropoisomerase I mutation, wherein an adenine at nucleotide 330998 of a *Mycoplasma hyopneumoniae* J strain sequence provided as SEQ ID NO: 5 is substituted by a guanine causing a tyrosine to histidine substitution in a protein encoded by the nucleic acid molecule;

a mutation in an intergenic sequence between a putative ISMHp1 transposase and a hypothetical protein, wherein a cytosine at nucleotide 379103 of a *Mycoplasma hyopneumoniae* J strain sequence provided as SEQ ID NO: 5 is substituted by a guanine;

a putative transposase truncated pseudo mutation, wherein a guanine at nucleotide 411019 of a *Mycoplasma hyopneumoniae* J strain sequence provided as SEQ ID NO: 5 is substituted by an adenine;

a mutation in a hypothetical protein, wherein a guanine at nucleotide 438867 of a *Mycoplasma hyopneumoniae* J strain sequence provided as SEQ ID NO: 5 is substituted by an adenine causing a glycine to glutamine substitution in a protein encoded by the nucleic acid molecule;

a putative ABC transporter permease protein mutation, wherein a cytosine at nucleotide 446756 of a *Mycoplasma hyopneumoniae* J strain sequence provided as SEQ ID NO: 5 is substituted by a adenine causing a leucine to isoleucine substitution in a protein encoded by the nucleic acid molecule;

a nicotinate phosphoribosyltransferase mutation, wherein a guanine at nucleotide 495301 of a *Mycoplasma hyopneumoniae* J strain sequence provided as SEQ ID NO: 5 is substituted by a thymine causing a glycine to cysteine substitution in a protein encoded by the nucleic acid molecule;

a mutation in a hypothetical protein, wherein a guanine at nucleotide 538653 of a *Mycoplasma hyopneumoniae* J strain sequence provided as SEQ ID NO: 5 is substituted by an adenine causing an alanine to valine substitution in a protein encoded by the nucleic acid molecule;

a mutation in a hypothetical protein, wherein a cytosine at nucleotide 550628 of a *Mycoplasma hyopneumoniae* J strain sequence provided as SEQ ID NO: 5 is substituted by an adenine causing a glycine to valine substitution in a protein encoded by the nucleic acid molecule;

a mutation in a hypothetical protein, wherein a guanine at nucleotide 554103 of a *Mycoplasma hyopneumoniae* J strain sequence provided as SEQ ID NO: 5 is substituted by an adenine causing a proline to leucine substitution in a protein encoded by the nucleic acid molecule;

a mutation in a hypothetical protein, wherein a guanine at nucleotide 555585 of a *Mycoplasma hyopneumoniae* J strain sequence provided as SEQ ID NO: 5 is substituted by a thymine causing a threonine to asparagine substitution in a protein encoded by the nucleic acid molecule;

a mutation in a hypothetical protein, wherein a guanine at nucleotide 583967 of a *Mycoplasma hyopneumoniae* J strain sequence provided as SEQ ID NO: 5 is substituted by a thymosine causing a glycine to valine substitution in a protein encoded by the nucleic acid molecule;

a mutation in a hypothetical protein, wherein a cytosine at nucleotide 599805 of a *Mycoplasma hyopneumoniae* J strain sequence provided as SEQ ID NO: 5 is substituted by an adenine causing an aspartate to tyrosine substitution in a protein encoded by the nucleic acid molecule;

a mutation in a hypothetical protein, wherein a cytosine at nucleotide 615445 of a *Mycoplasma hyopneumoniae* J strain sequence provided as SEQ ID NO: 5 is substituted by an adenine causing a serine to isoleucine substitution in a protein encoded by the nucleic acid molecule;

a putative PTS system N-acetylglucosmamine-specific II ABC component mutation, wherein a guanine at nucleotide 743961 of a *Mycoplasma hyopneumoniae* J strain sequence provided as SEQ ID NO: 5 is substituted by an adenine causing an alanine to valine substitution in a protein encoded by the nucleic acid molecule;

a leucyl-tRNA synthetase mutation, wherein a cytosine at nucleotide 848512 of a *Mycoplasma hyopneumoniae* J strain sequence provided as SEQ ID NO: 5 is substituted by a guanine causing a methionine to isoleucine substitution in a protein encoded by the nucleic acid molecule; and a 16S ribosomal RNA MHJ_0709 mutation, wherein an adenine at nucleotide 881437 of a *Mycoplasma hyopneumoniae* J strain sequence provided as SEQ ID NO: 5 is substituted by a guanine;

or assaying the sample comprising *Mycoplasma hyopneumoniae* bacteria for the presence or absence of a protein encoded by the nucleic acid molecule with the mutation, wherein the presence of the nucleic acid molecule with the mutation or the presence of the protein encoded by the nucleic acid molecule with the mutation indicates that the sample comprises the *Mycoplasma hyopneumoniae* bacterium strain ts-19.

2. The method of claim 1, in which the assay is for a mutation selected from:

a mutation in a hypothetical protein, wherein a guanine at nucleotide 10909 of a *Mycoplasma hyopneumoniae* J strain sequence provided as SEQ ID NO: 5 is substituted by an adenine causing an alanine to threonine substitution in a protein encoded by the nucleic acid molecule;

a mutation in a hypothetical protein, wherein a guanine at nucleotide 246307 of a *Mycoplasma hyopneumoniae* J strain sequence provided as SEQ ID NO: 5 is substituted by a thymine causing a glycine to cysteine substitution in a protein encoded by the nucleic acid molecule;

a DNA tropoisomerase I mutation, wherein an adenine at nucleotide 330948 of a *Mycoplasma hyopneumoniae* J strain sequence provided as SEQ ID NO: 5 is substituted by a guanine;

a DNA tropoisomerase I mutation, wherein an adenine at nucleotide 330998 of a *Mycoplasma hyopneumoniae* J strain sequence provided as SEQ ID NO: 5 is substituted by a guanine causing a tyrosine to histidine substitution in a protein encoded by the nucleic acid molecule; or a 16S ribosomal RNA MHJ_0709 mutation, wherein an adenine at nucleotide 881437 of a *Mycoplasma hyopneumoniae* J strain sequence provided as SEQ ID NO:5 is substituted by a guanine.

3. The method of claim 1, in which the assay comprises high resolution melt analysis.

4. The method of claim 1, wherein the *Mycoplasma hyopneumoniae* bacterium is present in a sample from an animal, and wherein the absence of the mutation indicates that the animal is infected with virulent *Mycoplasma hyopneumoniae.*

5. The method of claim 1, wherein the presence of the mutation indicates that the sample is from an animal vaccinated with a vaccine comprising *Mycoplasma hyopneumoniae* bacterium strain ts-19.

* * * * *